( 12 ) United States Patent
Takakura et al.

(10) Patent No.: US 8,304,236 B2
(45) Date of Patent: Nov. 6, 2012

(54) MODIFIED BIOTIN-BINDING PROTEIN

(75) Inventors: Yoshimitsu Takakura, Iwata (JP);
Masako Ichikawa, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 135 days.

(21) Appl. No.: 13/058,130

(22) PCT Filed: Aug. 13, 2009

(86) PCT No.: PCT/JP2009/064302
§ 371 (c)(1),
(2), (4) Date: Feb. 8, 2011

(87) PCT Pub. No.: WO2010/018859
PCT Pub. Date: Feb. 18, 2010

(65) Prior Publication Data
US 2011/0263824 A1    Oct. 27, 2011

(30) Foreign Application Priority Data
Aug. 13, 2008  (JP) .................................. 2008-208766

(51) Int. Cl.
C12N 15/00  (2006.01)
C07H 21/02  (2006.01)
C07K 14/00  (2006.01)
(52) U.S. Cl. .................... 435/320.1; 536/23.1; 530/350; 514/1
(58) Field of Classification Search .................. 530/350; 536/23.1; 435/320.1; 514/1
See application file for complete search history.

(56) References Cited

U.S. PATENT DOCUMENTS 7,713,531 B2 * 5/2010 Takakura .................. 424/184.1
7,855,282 B2 * 12/2010 Takakura .................... 536/23.7
2005/0089983 A1 4/2005 Takakura
2009/0187006 A1 7/2009 Takakura

FOREIGN PATENT DOCUMENTS

| CA | 2756109 A1 | 10/2010 |
| EP | 2112168 A1 | 10/2009 |
| EP | 2 267 119 A1 | 12/2010 |
| WO | WO 02/072817 A1 | 9/2002 |
| WO | WO 2008/081938 A1 | 7/2008 |
| WO | WO 2010/114031 A1 | 10/2010 |

OTHER PUBLICATIONS

Extended European Seach Report, dated Dec. 19, 2011, for European Application No. 09806750.7.
Kyte et al., "A Simple Method for Displaying the Hydropathic Character of a Protein", J. Mol. Biol., vol. 157, 1982, pp. 105-132.
Takakura et al., "Tamavidins—novel avidin-like biotin-binding proteins from the Tamogitake mushroom", The FEBS Journal, vol. 276, 2009, pp. 1383-1397, XP-002616627.
International Search Report, dated Oct. 20, 2009, issued in corresponding International Application PCT/JP2009/064302.
Alon et al., "Streptavidin Contains an RYD Sequence Which Mimics the RGD Receptor Domain of Fibronectin", Biochemical and Biophysical Research Communications, Aug. 16, 1990, vol. 170, No. 3, pp. 1236-1241.
Aslan et al., "Engineered single-chain dimeric streptavidins with an unexpected strong preference for biotin-4-fluorescein", Proceedings of the National Academy of Sciences of the United States of America, Jun. 14, 2005, vol. 102, No. 24, pp. 8507-8512 and vol. 102, No. 44, pp. 16119-16120.
Bayer et al., "Preparation of Deglycosylated Egg White Avidin", Applied Biochemistry and Biotechnology, 1995, vol. 53, pp. 1-9.
Laitinen et al., "Genetically engineered avidins and streptavidins", Cellular and Molecular Life Sciences, 2006, vol. 63, No. 24, pp. 2992-3017.
Livnah et al., "Three-dimensional structures of avidin and the avidin-biotin complex", Proceedings of the National Academy of Sciences of the United States of America, Jun. 1993, vol. 90, pp. 5076-5080.
Marttila et al., "Engineering of chicken avidin: a progressive series of reduced charge mutants", FEBS Letters, 1998, vol. 441, pp. 313-317.
Marttila et al., "Recombinant NeutraLite Avidin: a non-glycosylated, acidic mutant of chicken avidin that exhibits high affinity for biotin and low non-specific binding properties", FEBS Letters, 2000, vol. 467, pp. 31-36.
Qureshi et al., "Development and Characterization of a Series of Soluble Tetrameric and Monomeric Streptavidin Muteins with Differential Biotin Binding Affinities", The Journal of Biological Chemistry, Dec. 7, 2001, vol. 276, No. 49, pp. 46422-46428.
Weber et al., "Structural Origins of High-Affinity Biotin Binding to Streptavidin", Science, Jan. 6, 1989, vol. 243, pp. 85-88.
Wu et al., "Engineering Soluble Monomeric Streptavidin with Reversible Biotin Binding Capability", The Journal of Biological Chemistry, Jun. 17, 2005, vol. 280, No. 24, pp. 23225-23231.

* cited by examiner

Primary Examiner — Karen Cochrane Carlson
(74) Attorney, Agent, or Firm — Birch Stewart Kolasch & Birch, LLP

(57) ABSTRACT

The present invention relates to a modified biotin-binding protein. The modified biotin-binding protein of the present invention includes an amino acid sequence represented by SEQ ID NO: 2, an amino acid sequence having one to several amino acid mutations in the sequence represented by SEQ ID NO: 2, or an amino acid sequence having 80% or more identity to the sequence represented by SEQ ID NO: 2, and having a biotin-binding activity, wherein at least one residue selected from the group consisting of:
  1) an arginine residue at position 104 of SEQ ID NO: 2;
  2) a lysine residue at position 141 of SEQ ID NO: 2;
  3) a lysine residue at position 26 of SEQ ID NO: 2; and
  4) a lysine residue at position 73 of SEQ ID NO: 2
is replaced with an acidic amino acid residue or a neutral amino acid residue.

15 Claims, 3 Drawing Sheets

** p < 0.01 vs TM2

* p < 0.01 vs TM2

* p < 0.1 vs TM2

* p < 0.01 vs TM2

SEQUENCE LISTING

```
<160> NUMBER OF SEQ ID NOS: 39

<210> SEQ ID NO 1
<211> LENGTH: 840
<212> TYPE: DNA
<213> ORGANISM: Pleurotus cornucopiae
<220> FEATURE:
<221> NAME/KEY: CDS
<222> LOCATION: (226)..(651)

<400> SEQUENCE: 1
gtggactctt gcgcgggcag gtacattcac aggtcgtgca ggttgtggga gtattcagtg      60
gctcagactc ttgtgctgac gggtatagat tcacaagccg tgcaggttgt gggagtactc     120
agagggtgag tgattgaatg gaagcacatc ggcgctggtt tcaagccgag aattgaggaa     180
gtaatactcc aagccgatga gaggttacag agatcctcta ccacc atg tca gac gtt     237
                                                  Met Ser Asp Val
                                                  1 caa tct tca ctc acc gga acc tgg tac aat gaa ctc aac tcc aag atg       285
Gln Ser Ser Leu Thr Gly Thr Trp Tyr Asn Glu Leu Asn Ser Lys Met
5                   10                  15                  20 gaa ttg act gca aac aaa gac ggt act ctc act gga aag tac ctc tcc       333
Glu Leu Thr Ala Asn Lys Asp Gly Thr Leu Thr Gly Lys Tyr Leu Ser
                25                  30                  35 aaa gtt ggg gat gtc tac gtg ccc tac cca ctc tct ggt cgc tat aac       381
Lys Val Gly Asp Val Tyr Val Pro Tyr Pro Leu Ser Gly Arg Tyr Asn
            40                  45                  50 ctc caa ccc ccc gcg gga caa ggc gtc gct ctt ggg tgg gcg gta tcc       429
Leu Gln Pro Pro Ala Gly Gln Gly Val Ala Leu Gly Trp Ala Val Ser
        55                  60                  65 tgg gag aac agt aaa att cat tcc gct acg aca tgg agc gga cag ttc       477
Trp Glu Asn Ser Lys Ile His Ser Ala Thr Thr Trp Ser Gly Gln Phe
    70                  75                  80 ttc tct gag tcg tct cca gtg att ctt act cag tgg ttg ttg tca tcg       525
Phe Ser Glu Ser Ser Pro Val Ile Leu Thr Gln Trp Leu Leu Ser Ser
85                  90                  95                  100
```

```
agc act gcg cgt ggg gac gta tgg gaa tcc aca ctt gtg ggg aat gat    573
Ser Thr Ala Arg Gly Asp Val Trp Glu Ser Thr Leu Val Gly Asn Asp
            105                 110                 115 tcg ttt aca aag acg gcg ccg act gag cag cag atc gct cat gct caa    621
Ser Phe Thr Lys Thr Ala Pro Thr Glu Gln Gln Ile Ala His Ala Gln
        120                 125                 130 ctc cat tgt cgc gca ccg agg ttg aag taa cgagggtcat cgcaaacaaa      671
Leu His Cys Arg Ala Pro Arg Leu Lys
        135                 140 ccccatcggt cttgaccggt gatccaaccc caaggtctaa tcaatgccgg atgactccat  731
ttgaggatgt gaattagttg ccatttgtat gacttgattt gtctgttgtg tagtatcgga  791
ttaagaatca catctcgtta accttcaaaa aaaaaaaaaa aaaaaaaa              840

<210> SEQ ID NO 2
<211> LENGTH: 141
<212> TYPE: PRT
<213> ORGANISM: Pleurotus cornucopiae

<400> SEQUENCE: 2

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140

<210> SEQ ID NO 3
<211> LENGTH: 426
<212> TYPE: DNA
<213> ORGANISM: Artificial Sequence
<220> FEATURE:
<223> OTHER INFORMATION: Synthetic: TM2 K26A
<220> FEATURE:
<221> NAME/KEY: CDS
<222> LOCATION: (1)..(423)

<400> SEQUENCE: 3 atg tca gac gtt caa tct tca ctc acc gga acc tgg tac aat gaa ctc    48
Met Ser Asp Val Gln Ser Ser Leu Thr Gly Thr Trp Tyr Asn Glu Leu
1               5                   10                  15 aac tcc aag atg gaa ttg act gca aac gca gac ggt act ctc act gga    96
Asn Ser Lys Met Glu Leu Thr Ala Asn Ala Asp Gly Thr Leu Thr Gly
            20                  25                  30 aag tac ctc tcc aaa gtt ggg gat gtc tac gtg ccc tac cca ctc tct   144
Lys Tyr Leu Ser Lys Val Gly Asp Val Tyr Val Pro Tyr Pro Leu Ser
        35                  40                  45 ggt cgc tat aac ctc caa ccc ccc gcg gga caa ggc gtc gct ctt ggg   192
Gly Arg Tyr Asn Leu Gln Pro Pro Ala Gly Gln Gly Val Ala Leu Gly
```

```
              50                  55                  60
tgg gcg gta tcc tgg gag aac agt aaa att cat tcc gct acg aca tgg    240
Trp Ala Val Ser Trp Glu Asn Ser Lys Ile His Ser Ala Thr Thr Trp
 65                  70                  75                  80 agc gga cag ttc ttc tct gag tcg tct cca gtg att ctt act cag tgg    288
Ser Gly Gln Phe Phe Ser Glu Ser Ser Pro Val Ile Leu Thr Gln Trp
                 85                  90                  95 ttg ttg tca tcg agc act gcg cgt ggg gac gta tgg gaa tcc aca ctt    336
Leu Leu Ser Ser Ser Thr Ala Arg Gly Asp Val Trp Glu Ser Thr Leu
            100                 105                 110 gtg ggg aat gat tcg ttt aca aag acg gcg ccg act gag cag cag atc    384
Val Gly Asn Asp Ser Phe Thr Lys Thr Ala Pro Thr Glu Gln Gln Ile
        115                 120                 125 gct cat gct caa ctc cat tgt cgc gca ccg agg ttg aag taa            426
Ala His Ala Gln Leu His Cys Arg Ala Pro Arg Leu Lys
    130                 135                 140

<210> SEQ ID NO 4
<211> LENGTH: 141
<212> TYPE: PRT
<213> ORGANISM: Artificial Sequence
<220> FEATURE:
<223> OTHER INFORMATION: Synthetic: TM2 K26A

<400> SEQUENCE: 4

Met Ser Asp Val Gln Ser Ser Leu Thr Gly Thr Trp Tyr Asn Glu Leu
 1               5                  10                  15

Asn Ser Lys Met Glu Leu Thr Ala Asn Ala Asp Gly Thr Leu Thr Gly
                 20                  25                  30

Lys Tyr Leu Ser Lys Val Gly Asp Val Tyr Val Pro Tyr Pro Leu Ser
            35                  40                  45

Gly Arg Tyr Asn Leu Gln Pro Pro Ala Gly Gln Gly Val Ala Leu Gly
        50                  55                  60

Trp Ala Val Ser Trp Glu Asn Ser Lys Ile His Ser Ala Thr Thr Trp
 65                  70                  75                  80

Ser Gly Gln Phe Phe Ser Glu Ser Ser Pro Val Ile Leu Thr Gln Trp
                 85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140

<210> SEQ ID NO 5
<211> LENGTH: 426
<212> TYPE: DNA
<213> ORGANISM: Artificial Sequence
<220> FEATURE:
<223> OTHER INFORMATION: Synthetic: TM2 K73Q
<220> FEATURE:
<221> NAME/KEY: CDS
<222> LOCATION: (1)..(423)

<400> SEQUENCE: 5 atg tca gac gtt caa tct tca ctc acc gga acc tgg tac aat gaa ctc    48
Met Ser Asp Val Gln Ser Ser Leu Thr Gly Thr Trp Tyr Asn Glu Leu
 1               5                  10                  15 aac tcc aag atg gaa ttg act gca aac aaa gac ggt act ctc act gga    96
Asn Ser Lys Met Glu Leu Thr Ala Asn Lys Asp Gly Thr Leu Thr Gly
                 20                  25                  30
```

| | | |
|---|---|---|
| aag tac ctc tcc aaa gtt ggg gat gtc tac gtg ccc tac cca ctc tct<br>Lys Tyr Leu Ser Lys Val Gly Asp Val Tyr Val Pro Tyr Pro Leu Ser<br>             35                    40                   45 | 144 |
| ggt cgc tat aac ctc caa ccc ccc gcg gga caa ggc gtc gct ctt ggg<br>Gly Arg Tyr Asn Leu Gln Pro Pro Ala Gly Gln Gly Val Ala Leu Gly<br> 50                     55                   60 | 192 |
| tgg gcg gta tcc tgg gag aac agt caa att cat tcc gct acg aca tgg<br>Trp Ala Val Ser Trp Glu Asn Ser Gln Ile His Ser Ala Thr Thr Trp<br>65                   70                   75                   80 | 240 |
| agc gga cag ttc ttc tct gag tcg tct cca gtg att ctt act cag tgg<br>Ser Gly Gln Phe Phe Ser Glu Ser Ser Pro Val Ile Leu Thr Gln Trp<br>                  85                    90                   95 | 288 |
| ttg ttg tca tcg agc act gcg cgt ggg gac gta tgg gaa tcc aca ctt<br>Leu Leu Ser Ser Ser Thr Ala Arg Gly Asp Val Trp Glu Ser Thr Leu<br>             100                  105                110 | 336 |
| gtg ggg aat gat tcg ttt aca aag acg gcg ccg act gag cag cag atc<br>Val Gly Asn Asp Ser Phe Thr Lys Thr Ala Pro Thr Glu Gln Gln Ile<br>          115                  120                125 | 384 |
| gct cat gct caa ctc cat tgt cgc gca ccg agg ttg aag taa<br>Ala His Ala Gln Leu His Cys Arg Ala Pro Arg Leu Lys<br>         130                  135                140 | 426 |

<210> SEQ ID NO 6
<211> LENGTH: 141
<212> TYPE: PRT
<213> ORGANISM: Artificial Sequence
<220> FEATURE:
<223> OTHER INFORMATION: Synthetic: TM2 K73Q

<400> SEQUENCE: 6

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Gln Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140

<210> SEQ ID NO 7
<211> LENGTH: 426
<212> TYPE: DNA
<213> ORGANISM: Artificial Sequence
<220> FEATURE:
<223> OTHER INFORMATION: Synthetic: TM2 R104E
<220> FEATURE:
<221> NAME/KEY: CDS
<222> LOCATION: (1)..(423)

<400> SEQUENCE: 7

| | | |
|---|---|---|
| atg tca gac gtt caa tct tca ctc acc gga acc tgg tac aat gaa ctc<br>Met Ser Asp Val Gln Ser Ser Leu Thr Gly Thr Trp Tyr Asn Glu Leu | 48 |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| aac | tcc | aag | atg | gaa | ttg | act | gca | aac | aaa | gac | ggt | act | ctc | act | gga | 96 |
| Asn | Ser | Lys | Met | Glu | Leu | Thr | Ala | Asn | Lys | Asp | Gly | Thr | Leu | Thr | Gly | |
| | | | 20 | | | | | 25 | | | | | 30 | | | |
| aag | tac | ctc | tcc | aaa | gtt | ggg | gat | gtc | tac | gtg | ccc | tac | cca | ctc | tct | 144 |
| Lys | Tyr | Leu | Ser | Lys | Val | Gly | Asp | Val | Tyr | Val | Pro | Tyr | Pro | Leu | Ser | |
| | | | 35 | | | | | 40 | | | | | 45 | | | |
| ggt | cgc | tat | aac | ctc | caa | ccc | ccc | gcg | gga | caa | ggc | gtc | gct | ctt | ggg | 192 |
| Gly | Arg | Tyr | Asn | Leu | Gln | Pro | Pro | Ala | Gly | Gln | Gly | Val | Ala | Leu | Gly | |
| | 50 | | | | | 55 | | | | | 60 | | | | | |
| tgg | gcg | gta | tcc | tgg | gag | aac | agt | aaa | att | cat | tcc | gct | acg | aca | tgg | 240 |
| Trp | Ala | Val | Ser | Trp | Glu | Asn | Ser | Lys | Ile | His | Ser | Ala | Thr | Thr | Trp | |
| 65 | | | | | 70 | | | | | 75 | | | | | 80 | |
| agc | gga | cag | ttc | ttc | tct | gag | tcg | tct | cca | gtg | att | ctt | act | cag | tgg | 288 |
| Ser | Gly | Gln | Phe | Phe | Ser | Glu | Ser | Ser | Pro | Val | Ile | Leu | Thr | Gln | Trp | |
| | | | | 85 | | | | | 90 | | | | | 95 | | |
| ttg | ttg | tca | tcg | agc | act | gcg | gaa | ggg | gac | gta | tgg | gaa | tcc | aca | ctt | 336 |
| Leu | Leu | Ser | Ser | Ser | Thr | Ala | Glu | Gly | Asp | Val | Trp | Glu | Ser | Thr | Leu | |
| | | | | 100 | | | | | 105 | | | | | 110 | | |
| gtg | ggg | aat | gat | tcg | ttt | aca | aag | acg | gcg | ccg | act | gag | cag | cag | atc | 384 |
| Val | Gly | Asn | Asp | Ser | Phe | Thr | Lys | Thr | Ala | Pro | Thr | Glu | Gln | Gln | Ile | |
| | | | 115 | | | | | 120 | | | | | 125 | | | |
| gct | cat | gct | caa | ctc | cat | tgt | cgc | gca | ccg | agg | ttg | aag | taa | | | 426 |
| Ala | His | Ala | Gln | Leu | His | Cys | Arg | Ala | Pro | Arg | Leu | Lys | | | | |
| | 130 | | | | | 135 | | | | | 140 | | | | | |

<210> SEQ ID NO 8
<211> LENGTH: 141
<212> TYPE: PRT
<213> ORGANISM: Artificial Sequence
<220> FEATURE:
<223> OTHER INFORMATION: Synthetic: TM2 R104E

<400> SEQUENCE: 8

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Glu Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140

<210> SEQ ID NO 9
<211> LENGTH: 426
<212> TYPE: DNA
<213> ORGANISM: Artificial Sequence
<220> FEATURE:
<223> OTHER INFORMATION: Synthetic: TM2 K141E
<220> FEATURE:
<221> NAME/KEY: CDS

<222> LOCATION: (1)..(423)

<400> SEQUENCE: 9

```
atg tca gac gtt caa tct tca ctc acc gga acc tgg tac aat gaa ctc     48
Met Ser Asp Val Gln Ser Ser Leu Thr Gly Thr Trp Tyr Asn Glu Leu
 1               5                  10                  15 aac tcc aag atg gaa ttg act gca aac aaa gac ggt act ctc act gga     96
Asn Ser Lys Met Glu Leu Thr Ala Asn Lys Asp Gly Thr Leu Thr Gly
             20                  25                  30 aag tac ctc tcc aaa gtt ggg gat gtc tac gtg ccc tac cca ctc tct    144
Lys Tyr Leu Ser Lys Val Gly Asp Val Tyr Val Pro Tyr Pro Leu Ser
         35                  40                  45 ggt cgc tat aac ctc caa ccc ccc gcg gga caa ggc gtc gct ctt ggg    192
Gly Arg Tyr Asn Leu Gln Pro Pro Ala Gly Gln Gly Val Ala Leu Gly
     50                  55                  60 tgg gcg gta tcc tgg gag aac agt aaa att cat tcc gct acg aca tgg    240
Trp Ala Val Ser Trp Glu Asn Ser Lys Ile His Ser Ala Thr Thr Trp
 65                  70                  75                  80 agc gga cag ttc ttc tct gag tcg tct cca gtg att ctt act cag tgg    288
Ser Gly Gln Phe Phe Ser Glu Ser Ser Pro Val Ile Leu Thr Gln Trp
                 85                  90                  95 ttg ttg tca tcg agc act gcg cgt ggg gac gta tgg gaa tcc aca ctt    336
Leu Leu Ser Ser Ser Thr Ala Arg Gly Asp Val Trp Glu Ser Thr Leu
            100                 105                 110 gtg ggg aat gat tcg ttt aca aag acg gcg ccg act gag cag cag atc    384
Val Gly Asn Asp Ser Phe Thr Lys Thr Ala Pro Thr Glu Gln Gln Ile
        115                 120                 125 gct cat gct caa ctc cat tgt cgc gca ccg agg ttg gag taa            426
Ala His Ala Gln Leu His Cys Arg Ala Pro Arg Leu Glu
    130                 135                 140
```

<210> SEQ ID NO 10
<211> LENGTH: 141
<212> TYPE: PRT
<213> ORGANISM: Artificial Sequence
<220> FEATURE:
<223> OTHER INFORMATION: Synthetic: TM2 K141E

<400> SEQUENCE: 10

```
Met Ser Asp Val Gln Ser Ser Leu Thr Gly Thr Trp Tyr Asn Glu Leu
 1               5                  10                  15

Asn Ser Lys Met Glu Leu Thr Ala Asn Lys Asp Gly Thr Leu Thr Gly
             20                  25                  30

Lys Tyr Leu Ser Lys Val Gly Asp Val Tyr Val Pro Tyr Pro Leu Ser
         35                  40                  45

Gly Arg Tyr Asn Leu Gln Pro Pro Ala Gly Gln Gly Val Ala Leu Gly
     50                  55                  60

Trp Ala Val Ser Trp Glu Asn Ser Lys Ile His Ser Ala Thr Thr Trp
 65                  70                  75                  80

Ser Gly Gln Phe Phe Ser Glu Ser Ser Pro Val Ile Leu Thr Gln Trp
                 85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Glu
    130                 135                 140
```

<210> SEQ ID NO 11
<211> LENGTH: 426

<212> TYPE: DNA
<213> ORGANISM: Artificial Sequence
<220> FEATURE:
<223> OTHER INFORMATION: Synthetic: TM2 K33TK37A
<220> FEATURE:
<221> NAME/KEY: CDS
<222> LOCATION: (1)..(423)

<400> SEQUENCE: 11

```
atg tca gac gtt caa tct tca ctc acc gga acc tgg tac aat gaa ctc      48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga      96
Asn Ser Lys Met Glu Leu Thr Ala Asn Lys Asp Gly Thr Leu Thr Gly
            20                  25                  30 acg tac ctc tcc gca gtt ggg gat gtc tac gtg ccc tac cca ctc tct     144
Thr Tyr Leu Ser Ala Val Gly Asp Val Tyr Val Pro Tyr Pro Leu Ser
        35                  40                  45 ggt cgc tat aac ctc caa ccc ccc gcg gga caa ggc gtc gct ctt ggg     192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct acg aca tgg     240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg     288
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt     336
Leu Leu Ser Ser Ser Thr Ala Arg Gly Asp Val Trp Glu Ser Thr Leu
            100                 105                 110 gtg ggg aat gat tcg ttt aca aag acg gcg ccg act gag cag cag atc     384
Val Gly Asn Asp Ser Phe Thr Lys Thr Ala Pro Thr Glu Gln Gln Ile
        115                 120                 125 gct cat gct caa ctc cat tgt cgc gca ccg agg ttg aag taa             426
Ala His Ala Gln Leu His Cys Arg Ala Pro Arg Leu Lys
    130                 135                 140
```

<210> SEQ ID NO 12
<211> LENGTH: 141
<212> TYPE: PRT
<213> ORGANISM: Artificial Sequence
<220> FEATURE:
<223> OTHER INFORMATION: Synthetic: TM2 K33TK37A

<400> SEQUENCE: 12

```
Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Thr Tyr Leu Ser Ala Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125
```

```
Ala His Ala Gln Leu His Cys Arg Ala Pro Arg Leu Lys
    130                 135                 140

<210> SEQ ID NO 13
<211> LENGTH: 426
<212> TYPE: DNA
<213> ORGANISM: Artificial Sequence
<220> FEATURE:
<223> OTHER INFORMATION: Synthetic: TM2 K33TK37AR104E
<220> FEATURE:
<221> NAME/KEY: CDS
<222> LOCATION: (1)..(423)

<400> SEQUENCE: 13 atg tca gac gtt caa tct tca ctc acc gga acc tgg tac aat gaa ctc     48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga     96
Asn Ser Lys Met Glu Leu Thr Ala Asn Lys Asp Gly Thr Leu Thr Gly
            20                  25                  30 acg tac ctc tcc gca gtt ggg gat gtc tac gtg ccc tac cca ctc tct    144
Thr Tyr Leu Ser Ala Val Gly Asp Val Tyr Val Pro Tyr Pro Leu Ser
        35                  40                  45 ggt cgc tat aac ctc caa ccc ccc gcg gga caa ggc gtc gct ctt ggg    192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct acg aca tgg    240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg    288
Ser Gly Gln Phe Phe Ser Glu Ser Ser Pro Val Ile Leu Thr Gln Trp
                85                  90                  95 ttg ttg tca tcg agc act gcg gaa ggg gac gta tgg gaa tcc aca ctt    336
Leu Leu Ser Ser Ser Thr Ala Glu Gly Asp Val Trp Glu Ser Thr Leu
            100                 105                 110 gtg ggg aat gat tcg ttt aca aag acg gcg ccg act gag cag cag atc    384
Val Gly Asn Asp Ser Phe Thr Lys Thr Ala Pro Thr Glu Gln Gln Ile
        115                 120                 125 gct cat gct caa ctc cat tgt cgc gca ccg agg ttg aag taa            426
Ala His Ala Gln Leu His Cys Arg Ala Pro Arg Leu Lys
    130                 135                 140

<210> SEQ ID NO 14
<211> LENGTH: 141
<212> TYPE: PRT
<213> ORGANISM: Artificial Sequence
<220> FEATURE:
<223> OTHER INFORMATION: Synthetic: TM2 K33TK37AR104E

<400> SEQUENCE: 14

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Thr Tyr Leu Ser Ala Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95
```

```
Leu Leu Ser Ser Ser Thr Ala Glu Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140
```

<210> SEQ ID NO 15
<211> LENGTH: 426
<212> TYPE: DNA
<213> ORGANISM: Artificial Sequence
<220> FEATURE:
<223> OTHER INFORMATION: Synthetic: TM2 R104EK141E
<220> FEATURE:
<221> NAME/KEY: CDS
<222> LOCATION: (1)..(423)

<400> SEQUENCE: 15

```
atg tca gac gtt caa tct tca ctc acc gga acc tgg tac aat gaa ctc    48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga    96
Asn Ser Lys Met Glu Leu Thr Ala Asn Lys Asp Gly Thr Leu Thr Gly
            20                  25                  30 aag tac ctc tcc aaa gtt ggg gat gtc tac gtg ccc tac cca ctc tct    144
Lys Tyr Leu Ser Lys Val Gly Asp Val Tyr Val Pro Tyr Pro Leu Ser
        35                  40                  45 ggt cgc tat aac ctc caa ccc ccc gcg gga caa ggc gtc gct ctt ggg    192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct acg aca tgg    240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg    288
Ser Gly Gln Phe Phe Ser Glu Ser Ser Pro Val Ile Leu Thr Gln Trp
                85                  90                  95 ttg ttg tca tcg agc act gcg gaa ggg gac gta tgg gaa tcc aca ctt    336
Leu Leu Ser Ser Ser Thr Ala Glu Gly Asp Val Trp Glu Ser Thr Leu
            100                 105                 110 gtg ggg aat gat tcg ttt aca aag acg gcg ccg act gag cag cag atc    384
Val Gly Asn Asp Ser Phe Thr Lys Thr Ala Pro Thr Glu Gln Gln Ile
        115                 120                 125 gct cat gct caa ctc cat tgt cgc gca ccg agg ttg gag taa            426
Ala His Ala Gln Leu His Cys Arg Ala Pro Arg Leu Glu
    130                 135                 140
```

<210> SEQ ID NO 16
<211> LENGTH: 141
<212> TYPE: PRT
<213> ORGANISM: Artificial Sequence
<220> FEATURE:
<223> OTHER INFORMATION: Synthetic: TM2 R104EK141E

<400> SEQUENCE: 16

```
Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60
```

```
Trp Ala Val Ser Trp Glu Asn Ser Lys Ile His Ser Ala Thr Thr Trp
 65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Glu Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Glu
    130                 135                 140
```

<210> SEQ ID NO 17
<211> LENGTH: 426
<212> TYPE: DNA
<213> ORGANISM: Artificial Sequence
<220> FEATURE:
<223> OTHER INFORMATION: Synthetic: TM2 K19T
<220> FEATURE:
<221> NAME/KEY: CDS
<222> LOCATION: (1)..(423)

<400> SEQUENCE: 17

```
atg tca gac gtt caa tct tca ctc acc gga acc tgg tac aat gaa ctc      48
Met Ser Asp Val Gln Ser Ser Leu Thr Gly Thr Trp Tyr Asn Glu Leu
 1               5                  10                  15 aac tcc acg atg gaa ttg act gca aac aaa gac ggt act ctc act gga      96
Asn Ser Thr Met Glu Leu Thr Ala Asn Lys Asp Gly Thr Leu Thr Gly
                20                  25                  30 aag tac ctc tcc aaa gtt ggg gat gtc tac gtg ccc tac cca ctc tct     144
Lys Tyr Leu Ser Lys Val Gly Asp Val Tyr Val Pro Tyr Pro Leu Ser
            35                  40                  45 ggt cgc tat aac ctc caa ccc ccc gcg gga caa ggc gtc gct ctt ggg     192
Gly Arg Tyr Asn Leu Gln Pro Pro Ala Gly Gln Gly Val Ala Leu Gly
        50                  55                  60 tgg gcg gta tcc tgg gag aac agt aaa att cat tcc gct acg aca tgg     240
Trp Ala Val Ser Trp Glu Asn Ser Lys Ile His Ser Ala Thr Thr Trp
 65                  70                  75                  80 agc gga cag ttc ttc tct gag tcg tct cca gtg att ctt act cag tgg     288
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt     336
Leu Leu Ser Ser Ser Thr Ala Arg Gly Asp Val Trp Glu Ser Thr Leu
            100                 105                 110 gtg ggg aat gat tcg ttt aca aag acg gcg ccg act gag cag cag atc     384
Val Gly Asn Asp Ser Phe Thr Lys Thr Ala Pro Thr Glu Gln Gln Ile
        115                 120                 125 gct cat gct caa ctc cat tgt cgc gca ccg agg ttg aag taa             426
Ala His Ala Gln Leu His Cys Arg Ala Pro Arg Leu Lys
    130                 135                 140
```

<210> SEQ ID NO 18
<211> LENGTH: 141
<212> TYPE: PRT
<213> ORGANISM: Artificial Sequence
<220> FEATURE:
<223> OTHER INFORMATION: Synthetic: TM2 K19T

<400> SEQUENCE: 18

```
Met Ser Asp Val Gln Ser Ser Leu Thr Gly Thr Trp Tyr Asn Glu Leu
 1               5                  10                  15

Asn Ser Thr Met Glu Leu Thr Ala Asn Lys Asp Gly Thr Leu Thr Gly
                20                  25                  30
```

```
Lys Tyr Leu Ser Lys Val Gly Asp Val Tyr Val Pro Tyr Pro Leu Ser
         35                  40                  45

Gly Arg Tyr Asn Leu Gln Pro Pro Ala Gly Gln Gly Val Ala Leu Gly
 50                  55                  60

Trp Ala Val Ser Trp Glu Asn Ser Lys Ile His Ser Ala Thr Thr Trp
 65                  70                  75                  80

Ser Gly Gln Phe Phe Ser Glu Ser Ser Pro Val Ile Leu Thr Gln Trp
                 85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
130                 135                 140
```

<210> SEQ ID NO 19
<211> LENGTH: 426
<212> TYPE: DNA
<213> ORGANISM: Artificial Sequence
<220> FEATURE:
<223> OTHER INFORMATION: Synthetic: TM2 D40N
<220> FEATURE:
<221> NAME/KEY: CDS
<222> LOCATION: (1)..(423)

<400> SEQUENCE: 19

```
atg tca gac gtt caa tct tca ctc acc gga acc tgg tac aat gaa ctc      48
Met Ser Asp Val Gln Ser Ser Leu Thr Gly Thr Trp Tyr Asn Glu Leu
 1               5                  10                  15 aac tcc aag atg gaa ttg act gca aac aaa gac ggt act ctc act gga      96
Asn Ser Lys Met Glu Leu Thr Ala Asn Lys Asp Gly Thr Leu Thr Gly
             20                  25                  30 aag tac ctc tcc aaa gtt ggg aat gtc tac gtg ccc tac cca ctc tct     144
Lys Tyr Leu Ser Lys Val Gly Asn Val Tyr Val Pro Tyr Pro Leu Ser
         35                  40                  45 ggt cgc tat aac ctc caa ccc ccc gcg gga caa ggc gtc gct ctt ggg     192
Gly Arg Tyr Asn Leu Gln Pro Pro Ala Gly Gln Gly Val Ala Leu Gly
 50                  55                  60 tgg gcg gta tcc tgg gag aac agt aaa att cat tcc gct acg aca tgg     240
Trp Ala Val Ser Trp Glu Asn Ser Lys Ile His Ser Ala Thr Thr Trp
 65                  70                  75                  80 agc gga cag ttc ttc tct gag tcg tct cca gtg att ctt act cag tgg     288
Ser Gly Gln Phe Phe Ser Glu Ser Ser Pro Val Ile Leu Thr Gln Trp
                 85                  90                  95 ttg ttg tca tcg agc act gcg cgt ggg gac gta tgg gaa tcc aca ctt     336
Leu Leu Ser Ser Ser Thr Ala Arg Gly Asp Val Trp Glu Ser Thr Leu
            100                 105                 110 gtg ggg aat gat tcg ttt aca aag acg gcg ccg act gag cag cag atc     384
Val Gly Asn Asp Ser Phe Thr Lys Thr Ala Pro Thr Glu Gln Gln Ile
        115                 120                 125 gct cat gct caa ctc cat tgt cgc gca ccg agg ttg aag taa             426
Ala His Ala Gln Leu His Cys Arg Ala Pro Arg Leu Lys
130                 135                 140
```

<210> SEQ ID NO 20
<211> LENGTH: 141
<212> TYPE: PRT
<213> ORGANISM: Artificial Sequence
<220> FEATURE:
<223> OTHER INFORMATION: Synthetic: TM2 D40N

<400> SEQUENCE: 20

```
Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asn Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Thr Ala Arg Gly Asp Val Trp Glu Ser Thr Leu
                100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140

<210> SEQ ID NO 21
<211> LENGTH: 426
<212> TYPE: DNA
<213> ORGANISM: Artificial Sequence
<220> FEATURE:
<223> OTHER INFORMATION: Synthetic: TM2 D40NR104E
<220> FEATURE:
<221> NAME/KEY: CDS
<222> LOCATION: (1)..(423)

<400> SEQUENCE: 21 atg tca gac gtt caa tct tca ctc acc gga acc tgg tac aat gaa ctc      48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga      96
Asn Ser Lys Met Glu Leu Thr Ala Asn Lys Asp Gly Thr Leu Thr Gly
            20                  25                  30 aag tac ctc tcc aaa gtt ggg aat gtc tac gtg ccc tac cca ctc tct     144
Lys Tyr Leu Ser Lys Val Gly Asn Val Tyr Val Pro Tyr Pro Leu Ser
        35                  40                  45 ggt cgc tat aac ctc caa ccc ccc gcg gga caa ggc gtc gct ctt ggg     192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct acg aca tgg     240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg     288
Ser Gly Gln Phe Phe Ser Glu Ser Ser Pro Val Ile Leu Thr Gln Trp
                85                  90                  95 ttg ttg tca tcg agc act gcg gaa ggg gac gta tgg gaa tcc aca ctt     336
Leu Leu Ser Ser Ser Thr Ala Glu Gly Asp Val Trp Glu Ser Thr Leu
                100                 105                 110 gtg ggg aat gat tcg ttt aca aag acg gcg ccg act gag cag cag atc     384
Val Gly Asn Asp Ser Phe Thr Lys Thr Ala Pro Thr Glu Gln Gln Ile
        115                 120                 125 gct cat gct caa ctc cat tgt cgc gca ccg agg ttg aag taa             426
Ala His Ala Gln Leu His Cys Arg Ala Pro Arg Leu Lys
    130                 135                 140

<210> SEQ ID NO 22
<211> LENGTH: 141
<212> TYPE: PRT
```

<213> ORGANISM: Artificial Sequence
<220> FEATURE:
<223> OTHER INFORMATION: Synthetic: TM2 D40NR104E

<400> SEQUENCE: 22

```
Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asn Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Glu Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140
```

<210> SEQ ID NO 23
<211> LENGTH: 426
<212> TYPE: DNA
<213> ORGANISM: Artificial Sequence
<220> FEATURE:
<223> OTHER INFORMATION: Synthetic: TM2 D40NR104EK141E
<220> FEATURE:
<221> NAME/KEY: CDS
<222> LOCATION: (1)..(423)

<400> SEQUENCE: 23

```
atg tca gac gtt caa tct tca ctc acc gga acc tgg tac aat gaa ctc      48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga      96
Asn Ser Lys Met Glu Leu Thr Ala Asn Lys Asp Gly Thr Leu Thr Gly
            20                  25                  30 aag tac ctc tcc aaa gtt ggg aat gtc tac gtg ccc tac cca ctc tct     144
Lys Tyr Leu Ser Lys Val Gly Asn Val Tyr Val Pro Tyr Pro Leu Ser
        35                  40                  45 ggt cgc tat aac ctc caa ccc ccc gcg gga caa ggc gtc gct ctt ggg     192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct acg aca tgg     240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg     288
Ser Gly Gln Phe Phe Ser Glu Ser Ser Pro Val Ile Leu Thr Gln Trp
                85                  90                  95 ttg ttg tca tcg agc act gcg gaa ggg gac gta tgg gaa tcc aca ctt     336
Leu Leu Ser Ser Ser Thr Ala Glu Gly Asp Val Trp Glu Ser Thr Leu
            100                 105                 110 gtg ggg aat gat tcg ttt aca aag acg gcg ccg act gag cag cag atc     384
Val Gly Asn Asp Ser Phe Thr Lys Thr Ala Pro Thr Glu Gln Gln Ile
        115                 120                 125 gct cat gct caa ctc cat tgt cgc gca ccg agg ttg gag taa             426
Ala His Ala Gln Leu His Cys Arg Ala Pro Arg Leu Glu
    130                 135                 140
```

<210> SEQ ID NO 24
<211> LENGTH: 141
<212> TYPE: PRT
<213> ORGANISM: Artificial Sequence
<220> FEATURE:
<223> OTHER INFORMATION: Synthetic: TM2 D40NR104EK141E

<400> SEQUENCE: 24

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asn Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Glu Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Glu
    130                 135                 140

<210> SEQ ID NO 25
<211> LENGTH: 141
<212> TYPE: PRT
<213> ORGANISM: Artificial Sequence
<220> FEATURE:
<223> OTHER INFORMATION: Synthetic: TM2 D40NK141E

<400> SEQUENCE: 25

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asn Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Glu
    130                 135                 140

<210> SEQ ID NO 26
<211> LENGTH: 25
<212> TYPE: DNA

```
<213> ORGANISM: Artificial Sequence
<220> FEATURE:
<223> OTHER INFORMATION: Synthetic: primer for PCR Tm2NtermPci

<400> SEQUENCE: 26
aaaacatgtc agacgttcaa tcttc                                          25

<210> SEQ ID NO 27
<211> LENGTH: 28
<212> TYPE: DNA
<213> ORGANISM: Artificial Sequence
<220> FEATURE:
<223> OTHER INFORMATION: Synthetic: primer for PCR Tm2CtermBam

<400> SEQUENCE: 27
tttggatcct tacttcaacc tcggtgcg                                       28

<210> SEQ ID NO 28
<211> LENGTH: 108
<212> TYPE: DNA
<213> ORGANISM: Artificial Sequence
<220> FEATURE:
<223> OTHER INFORMATION: Synthetic: primer for PCR Tm2 K26A PciI FW

<400> SEQUENCE: 28 tttttttacat gtcagacgtt caatcttcac tcaccggaac ctggtacaat gaactcaact    60
ccaagatgga attgactgca aacgcagacg gtactctcac tggaaagt                108

<210> SEQ ID NO 29
<211> LENGTH: 33
<212> TYPE: DNA
<213> ORGANISM: Artificial Sequence
<220> FEATURE:
<223> OTHER INFORMATION: Synthetic: primer for PCR Tm2 K73Q F

<400> SEQUENCE: 29
tcctgggaga acagtcaaat tcattccgct acg                                 33

<210> SEQ ID NO 30
<211> LENGTH: 33
<212> TYPE: DNA
<213> ORGANISM: Artificial Sequence
<220> FEATURE:
<223> OTHER INFORMATION: Synthetic: primer for PCR Tm2 K73Q R

<400> SEQUENCE: 30
cgtagcggaa tgaatttgac tgttctccca gga                                 33

<210> SEQ ID NO 31
<211> LENGTH: 39
<212> TYPE: DNA
<213> ORGANISM: Artificial Sequence
<220> FEATURE:
<223> OTHER INFORMATION: Synthetic: primer for PCR Tm2 K33,37TA F

<400> SEQUENCE: 31
actctcactg gaacgtacct ctccgcagtt ggggatgtc                           39

<210> SEQ ID NO 32
<211> LENGTH: 39
<212> TYPE: DNA
<213> ORGANISM: Artificial Sequence
<220> FEATURE:
<223> OTHER INFORMATION: Synthetic: primer for PCR Tm2 K33,37TA R

<400> SEQUENCE: 32
```

```
gacatcccca actgcggaga ggtacgttcc agtgagagt              39
```

<210> SEQ ID NO 33
<211> LENGTH: 27
<212> TYPE: DNA
<213> ORGANISM: Artificial Sequence
<220> FEATURE:
<223> OTHER INFORMATION: Synthetic: primer for PCR Tm2 R104E F

<400> SEQUENCE: 33

```
tcgagcactg cggaagggga cgtatgg                           27
```

<210> SEQ ID NO 34
<211> LENGTH: 27
<212> TYPE: DNA
<213> ORGANISM: Artificial Sequence
<220> FEATURE:
<223> OTHER INFORMATION: Synthetic: primer for PCR Tm2 R104E R

<400> SEQUENCE: 34

```
ccatacgtcc ccttccgcag tgctcga                           27
```

<210> SEQ ID NO 35
<211> LENGTH: 30
<212> TYPE: DNA
<213> ORGANISM: Artificial Sequence
<220> FEATURE:
<223> OTHER INFORMATION: Synthetic: primer for PCR Tm2 K141E Bam

<400> SEQUENCE: 35

```
tttggatcct tactccaacc tcggtgcgcg                        30
```

<210> SEQ ID NO 36
<211> LENGTH: 27
<212> TYPE: DNA
<213> ORGANISM: Artificial Sequence
<220> FEATURE:
<223> OTHER INFORMATION: Synthetic: primer for PCR Tm2 K19T F

<400> SEQUENCE: 36

```
gaactcaact ccacgatgga attgact                           27
```

<210> SEQ ID NO 37
<211> LENGTH: 27
<212> TYPE: DNA
<213> ORGANISM: Artificial Sequence
<220> FEATURE:
<223> OTHER INFORMATION: Synthetic: primer for PCR Tm2 K19T R

<400> SEQUENCE: 37

```
agtcaattcc atcgtggagt tgagttc                           27
```

<210> SEQ ID NO 38
<211> LENGTH: 39
<212> TYPE: DNA
<213> ORGANISM: Artificial Sequence
<220> FEATURE:
<223> OTHER INFORMATION: Synthetic: primer for PCR TM2 SA D40N F

<400> SEQUENCE: 38

```
tacctctcca agttgggaa tgtctacgtg ccctaccca               39
```

<210> SEQ ID NO 39
<211> LENGTH: 39
<212> TYPE: DNA
<213> ORGANISM: Artificial Sequence
<220> FEATURE:

```
<223> OTHER INFORMATION: Synthetic: primer for PCR TM2 SA D40N R

<400> SEQUENCE: 39
tgggtagggc acgtagacat tcccaacttt ggagaggta                         39
```

MODIFIED BIOTIN-BINDING PROTEIN

TECHNICAL FIELD

This application claims priority of Japanese Patent Application No. 2008-208766 filed on Aug. 13, 2008.

The present invention relates to a modified biotin-binding protein.

BACKGROUND ART

Avidin is a protein derived from egg white, and streptavidin is a protein derived from *Streptomyces avidinii*. Avidin and streptavidin each have significantly high affinity ($KD=10^{-16}$ to $10^{-14}$) to biotin (D-[(+)-cis-hexahydro-2-oxo-1H-thieno-(3,4)-imidazole-4-valerate]), and the affinity is one of the most strong interactions between two biological molecules. Their molecular weights are about 60 kDa. Currently, the avidin/streptavidin-biotin interaction is widely applied to the fields of biochemistry, molecular biology, and medicine (Green, (1975), Adv. Protein Chem., 29: 85-133; Green, (1990), Methods Enzymol., 184: 51-67). Avidin and streptavidin each form a tetramer, and one subunit of the tetramer binds to one biotin molecule.

A problem in the use of avidin is non-specific binding thereof. Avidin may non-specifically bind to not only cells but also DNAs, proteins, and biological materials such as membranes. For example, in detection of a material using the avidin-biotin binding, avidin non-specifically binds to materials other than the object material to be detected to increase the background. The reasons for the high non-specific binding of avidin include its high isoelectric point and sugar chains contained in an amount of approximately 10% of the molecular weight. Avidin is a strongly basic protein, having a significantly high isoelectric point of 10 or more, and is positively charged as a whole. Accordingly, it is believed that avidin readily binds to biological materials, which are negatively charged in many cases.

In addition, it is believed that the sugar chains on the surface of avidin easily bind to biological materials (Marttila et al., (2000) FEBS Lett, 467, 31-36). In order to reduce the non-specific binding of avidin, there have been studies on, for example, chemically modified neutravidin in which sugar chains of avidin are removed by glycosidase (Bayer, et al., (1995) Appl Biochem Biotechnol, 53(1), 1-9) and biosynthesis of avidin not receiving sugar chain modification by replacing the asparagine residue at position 17 (a target of glycosilation in avidin), with an isoleucine residue (Marttila, et al., (2000) FEBS Lett, 467, 31-36). In addition, there is a study for reducing the isoelectric point of avidin by converting a lysine residue or an arginine residue of avidin into a neutral amino acid or an acidic amino acid by genetic engineering (Marttila, et al., (1998) FEBS Lett, 441, 313-317).

Although these modifications can reduce non-specific binding of, for example, DNAs and cells to avidin, a reduction in non-specific binding to human sera, which are necessarily used in clinical assay systems, has not been sufficiently investigated. In addition, biosynthesis of avidin mutants needs insect cell expression systems. Accordingly, sequence modification of avidin requires long culture times and high costs and, therefore, has not been put into practical use yet.

According to a reported study relating to affinity between biotin and a biotin-binding protein, such as avidin or streptavidin, binding with fluorescent biotin is strengthened by highly modifying the structure of streptavidin (Aslan, et al., (2005) Proc Natl Acad Sci U.S.A., 102, 8507-8512). Unfortunately, the biotin-binding ability of this protein is severely decreased.

The present inventors purified a protein showing antibacterial activity against *Magnaporthe grisea* from an edible mushroom, *Pleurotus cornucopiae*. The protein was revealed to have a biotin-binding activity and was named tamavidin (tamavidin 1). Both the amino acid sequence of the tamavidin 1 protein and the nucleotide sequence of a gene encoding the protein are disclosed in WO 02/072817 (SEQ ID NOs: 1 and 2 in WO02/072817). A homologue (tamavidin 2) of tamavidin 1 was also identified from *Plueurotus cornucopiae* and was shown to have strong biotin-binding ability. Both the amino acid sequence of the tamavidin 2 protein and the nucleotide sequence of a gene encoding the protein are disclosed in WO 02/072817 (SEQ ID NOs: 3 and 4 in WO02/072817), and a recombinant protein thereof has been successfully produced. Tamavidins 1 and 2 can be expressed in *Escherichia coli*. In particular, tamavidin 2, which can be easily prepared by purification using an iminobiotin column and has higher heat resistance than that of streptavidin, is an excellent biotin-binding protein. However, although the non-specific binding of tamavidin 2 to nucleic acids and/or proteins is lower than that of existing avidin, it is comparable with that of streptavidin.

CITATION LIST

Patent Document

Patent Document 1: WO02/072817 A1
Patent Document 2: WO2008/081938 A1

Non Patent Document

Non-Patent Document 1: Marttila, et al., (2000) FEBS Lett, 467, 31-36
Non-Patent Document 2: Bayer, et al., (1995) Appl Biochem Biotechnol, 53(1), 1-9
Non-Patent Document 3: Marttila, et al., (1998) FEBS Lett, 441, 313-317
Non-Patent Document 4: Alon, et al., (1990) Biochem Biophys Res Commun, 170, 1236-1241
Non-Patent Document 5: Aslan, et al., (2005) Proc Natl Acad Sci U.S.A., 102, 8507-8512
Non-Patent Document 6: Weber, et al., (1989) Science, 243: 85-88
Non-Patent Document 7: Livnah, et al., (1993) Proc. Natl. Acad. Sci. U.S.A., 90, 5076-5080
Non-Patent Document 8: Qureshi, et al., (2001) J. Biol. Chem., 276(49), pp. 46422-46428

SUMMARY OF INVENTION

Technical Problem

It is an object of the present invention to provide a modified biotin-binding protein that exhibits improved characteristics, such as reduced non-specific binding and/or further enhanced biotin-binding affinity, while retaining the specific characteristic of tamavidin, i.e., high biotin-binding ability.

Solution to Problem

The present invention has successfully improved the characteristics of tamavidin 2 (hereinafter, in this description, may be referred to as "TM2") by modifying the amino acid sequence (SEQ ID NO: 2) of natural tamavidin 2.

Preferred Embodiments of the Present Invention

The present invention preferably includes the following embodiments:

[Mode 1]

A modified biotin-binding protein, comprising an amino acid sequence represented by SEQ ID NO: 2, an amino acid sequence having one to several amino acid mutations in the sequence represented by SEQ ID NO: 2, or an amino acid sequence having 80% or more identity to the sequence represented by SEQ ID NO: 2, and having a biotin-binding activity, wherein
one or more residue(s) selected from
1) an arginine residue at position 104 of SEQ ID NO: 2;
2) a lysine residue at position 141 of SEQ ID NO: 2;
3) a lysine residue at position 26 of SEQ ID NO: 2; and
4) a lysine residue at position 73 of SEQ ID NO: 2
is replaced with an acidic amino acid residue or a neutral amino acid residue;

[Mode 2]

The modified biotin-binding protein according to mode 1, wherein the amino acid residue selected from 1) to 4) is replaced with an amino acid residue having a hydropathy index of 2 or less;

[Mode 3]

The modified biotin-binding protein according to mode 1, wherein 1) an arginine residue at position 104 of SEQ ID NO: 2 and/or 2) a lysine residue at position 141 of SEQ ID NO: 2 is replaced with an acidic amino acid residue or a neutral amino acid residue;

[Mode 4]

The modified biotin-binding protein according to mode 3, wherein 1) an arginine residue at position 104 of SEQ ID NO: 2 and/or 2) a lysine residue at position 141 of SEQ ID NO: 2 is replaced with an acidic amino acid residue;

[Mode 5]

The modified biotin-binding protein according to mode 3 or 4, wherein 1) an arginine residue at position 104 of SEQ ID NO: 2 and/or 2) a lysine residue at position 141 of SEQ ID NO: 2 is replaced with a glutamic acid residue;

[Mode 6]

The modified biotin-binding protein according to any one of modes 1 to 5, wherein an aspartic acid residue at position 40 of SEQ ID NO: 2 is replaced with an asparagine residue;

[Mode 7]

The modified biotin-binding protein according to any one of modes 1 to 6, which is selected from the group consisting of:
a modified biotin-binding protein (R104E-K141E) in which an arginine residue at position 104 of SEQ ID NO: 2 is replaced with a glutamic acid residue, and a lysine residue at position 141 is replaced with a glutamic acid residue;
a modified biotin-binding protein (D40N-R104E) in which an aspartic acid residue at position 40 of SEQ ID NO: 2 is replaced with an asparagine residue, and an arginine residue at position 104 is replaced with a glutamic acid residue;
a modified biotin-binding protein (D40N-K141E) in which an aspartic acid residue at position 40 of SEQ ID NO: 2 is replaced with an asparagine residue, and a lysine residue at position 141 is replaced with a glutamic acid residue; and
a modified biotin-binding protein (D40N-R104E-K141E) in which an aspartic acid residue at position 40 of SEQ ID NO: 2 is replaced with an asparagine residue, an arginine residue at position 104 is replaced with a glutamic acid residue, and a lysine residue at position 141 is replaced with a glutamic acid residue;

[Mode 8]

The modified biotin-binding protein according to any one of modes 1 to 7, which satisfies at least one requirement selected from the following requirements a) to l):
a) an asparagine residue at position 14 of SEQ ID NO: 2 is not modified or is replaced with glutamine or aspartic acid;
b) a serine residue at position 18 of SEQ ID NO: 2 is not modified or is replaced with threonine or tyrosine;
c) a tyrosine residue at position 34 of SEQ ID NO: 2 is not modified or is replaced with serine, threonine, or phenylalanine;
d) a serine residue at position 36 of SEQ ID NO: 2 is not modified or is replaced with threonine or tyrosine;
e) an aspartic acid residue at position 40 of SEQ ID NO: 2 is not modified or is replaced with asparagine;
f) a tryptophan residue at position 69 of SEQ ID NO: 2 is not modified;
g) a serine residue at position 76 of SEQ ID NO: 2 is not modified or is replaced with threonine or tyrosine;
h) a threonine residue at position 78 of SEQ ID NO: 2 is not modified or is replaced with serine or tyrosine;
i) a tryptophan residue at position 80 of SEQ ID NO: 2 is not modified;
j) a tryptophan residue at position 96 of SEQ ID NO: 2 is not modified;
k) a tryptophan residue at position 108 of SEQ ID NO: 2 is not modified; and
l) an aspartic acid residue at position 116 of SEQ ID NO: 2 is not modified or is replaced with glutamic acid or asparagine;

[Mode 9]

The modified biotin-binding protein according to mode 1, comprising an amino acid sequence having 90% or more identity to the sequence represented by SEQ ID NO: 2;

[Mode 10]

The modified biotin-binding protein according to any one of modes 1 to 9, which satisfies at least one property selected from the following properties i) to iv):
i) having an isoelectric point lower than that of a protein consisting of an amino acid sequence represented by SEQ ID NO: 2;
ii) showing less non-specific binding to nucleic acids and/or proteins compared to a protein consisting of an amino acid sequence represented by SEQ ID NO: 2;
iii) showing less fibronectin-binding activity compared to a protein consisting of an amino acid sequence represented by SEQ ID NO: 2; and
iv) to show more biotin-binding activity compared to a protein consisting of an amino acid sequence represented by SEQ ID NO: 2;

[Mode 11]

A modified biotin-binding protein, comprising an amino acid sequence represented by SEQ ID NO: 2, an amino acid sequence having one to several amino acid mutations in the sequence represented by SEQ ID NO: 2, or an amino acid sequence having 80% or more identity to the sequence represented by SEQ ID NO: 2, and having a biotin-binding activity, wherein an aspartic acid residue at position 40 of SEQ ID NO: 2 is replaced with an asparagine residue;

[Mode 12]

The modified biotin-binding protein according to mode 11, wherein the biotin-binding activity is higher than that of a protein consisting of the amino acid sequence represented by SEQ ID NO: 2;

[Mode 13]

A nucleic acid encoding the protein according to any one of modes 1 to 12;

[Mode 14]

A vector containing the nucleic acid according to mode 13; and

[Mode 15]

A carrier to which the protein according to any one of modes 1 to 12 is immobilized.

Preferred embodiments for implementing the present invention will be described below.

Tamavidin

Tamavidins are novel biotin-binding proteins that were discovered from an edible mushroom, *Pleurotus cornucopiae* (WO 02/072817). This document shows:

that tamavidin 1 and tamavidin 2 have an amino acid homology of 65.5% with each other and bind strongly to biotin;

that tamavidin 2 is highly expressed in *Escherichia coli* in soluble fractions; and that when tamavidin 2 was expressed in *Escherichia coli*, 4.5-hr culture gave a purified recombinant protein of high purity in an amount of about 1 mg per 50 ml of culture; this is a very high value, even greater than those for avidin and streptavidin which are known as biotin-binding proteins.

The term "tamavidin 2" as used herein means tamavidin 2 (TM2) or variants thereof. The present invention provides a modified TM2 that shows lower non-specific binding to nucleic acids and/or proteins than that of the wild type TM2 by modifying a specific amino acid residue of TM2 or variants thereof. In the present specification, "tamavidin 2" and "TM2" refer to the wild type TM2 or its variants, unless specified otherwise. However, these terms may be used as a generic name, including the modified TM2 of the present invention, wild type, variant-type, and modified-type of TM2, depending on the context. In addition, since TM2 shows biotin binding activity, it may be referred to as "biotin-binding protein" in the present specification. Specifically, TM2 (wild-type) may be typically a protein comprising an amino acid sequence of SEQ ID NO: 2 or a protein encoded by a nucleic acid comprising a nucleotide sequence of SEQ ID NO: 1. Alternatively, the TM2 may be a variant of the protein comprising an amino acid sequence of SEQ ID NO: 2 or variants of the protein encoded by a nucleic acid comprising a nucleotide sequence of SEQ ID NO: 1, wherein the variants have biotin-binding activities equivalent to that of tamavidin 2. The TM2 variants may be a protein comprising an amino acid sequence with deletion, substitution, insertion, and/or addition of one or more amino acids to the amino acid sequence of SEQ ID NO: 2 in which having and having a biotin-binding activity equivalent to that of TM2. Substitution may be conservative substitution, which means the replacement of a certain amino acid residue by another residue having similar physical and chemical characteristics. Non-limiting examples of conservative substitution include substitution of one aliphatic-group containing amino acid residue (e.g., Ile, Val, Leu or Ala) for another, and substitution of one polar residue for another, as between Lys and Arg, or Glu and Asp, or Gln and Asn.

The variants or mutants due to amino acid deletions, substitutions, insertions and/or additions can be prepared from the native protein encoding DNA by applying a well-known technique, say, site-specific mutagenesis (see, for example, Nucleic Acid Research, Vol. 10, No. 20, p. 6487-6500, 1982, which is incorporated herein by reference in its entirety). As used herein, the expression "one or more amino acids" means a feasible number of amino acids that can be deleted, substituted, inserted and/or added by site-specific mutagenesis. It should also be noted that the expression "one or more amino acids" as used herein may sometimes mean one or several amino acids.

Site-specific mutagenesis may be performed as follows using synthetic oligonucleotide primers that are complementary to the single-stranded phage DNA to be mutated, except for a specific mismatch that corresponds to the desirable mutation. To be more specific, the above-mentioned synthetic oligonucleotides are used as primers to synthesize a strand complementary to the phage and a host cell is transformed with the resulting double-stranded DNA. A culture of the transformed cell is plated on agar and plaques are formed from the phage-containing single cells. Then, theoretically, 50% of the new colonies contain phages having a mutation in a single strand and the remaining 50% have the original sequence. The obtained plaques are hybridized with a synthetic probe, as labeled by kinase treatment, at a temperature that allows for hybridization with those colonies that exhibit complete match with DNA having the above-mentioned desirable mutation but that does not allow for hybridization with those colonies having the original strand. Subsequently, plaques that hybridize with that probe are picked and cultured for DNA recovery.

Note that the methods of introducing deletion, substitution, insertion and/or addition of one or more amino acids in the amino acid sequence of a biologically active peptide while retaining its activity include not only the above-described site-specific mutagenesis but also a method that involves treating the gene with a mutagen, as well as a method that comprises cleaving the gene selectively, then removing, substituting, inserting or adding the chosen nucleotide, and finally linking the cleaved fragments. More preferably, TM2 as used in the present invention is a protein that consists of an amino acid sequence with deletion, substitution, insertion or addition of one to ten amino acids in the amino acid sequence of SEQ ID NO:2 and which has biotin-binding activity.

The variant or mutant of TM2 may also be a protein that comprises an amino acid sequence having at least 80% identical, preferably at least 85% identical, at least 90% identical, at least 95% identical, at least 96% identical, at least 97% identical, at least 98% identical, or at least 99% identical, and more preferably at least 99.3% identical, to the amino acid sequence of SEQ ID NO:2 and which has the similar biotin-binding activity as TM2 has.

Percent identity between two amino acid sequences may be determined by visual inspection and mathematical calculation. Alternatively, the percent identity of two protein sequences can be determined by comparing sequence information using the GAP computer program that is based on the algorithm of Needleman, S. B. and Wunsch, C. D. (J. Mol. Biol., 48: 443-453, 1970) and which is available from the University of Wisconsin Genetics Computer Group (UWGCG). The preferred default parameters for the GAP program include: (1) a scoring matrix, blosum 62, as described by Henikoff, S. and Henikoff, J. G. (Proc. Natl. Acad. Sci. USA 89: 10915-10919, 1992); (2) a gap weight of 12; (3) a gap length weight of 4; and (4) no penalty for end gaps.

Other programs used by skilled artisans for sequence comparison may also be used. Percent identity can be determined by comparison with sequence information using the BLAST program descried in, for example, Altschul et al. (Nucl. Acids. Res., 25, p. 3389-3402, 1997). This program can be accessed from the Internet at the website of the National Center for Biotechnology Information (NCBI) or the DNA Data Bank of Japan (DDBJ). Various conditions (parameters) for identity search by the BLAST program are detailed at those websites and part of the settings can be varied as appropriate, although search is typically performed using the default values. Alternatively, percent identity between two amino acid sequences may be determined by a program such as the genetic information processing software GENETYX Ver. 7 (Genetyx) or the FASTA algorithm. In this alternative case, search may be performed using the default values.

The percent identity of two nucleic acid sequences may be determined by visual inspection and mathematical calculation, or more preferably by comparing sequence information using a computer program. A typical, preferred computer program is the Wisconsin package, the program GAP of version 10.0, of Genetics Computer Group (GCG; Madison, State of Wisconsin) (Devereux et al., Nucl. Acids Res. 12: 387, 1984). Using this program GAP, one can perform comparison not only between two nucleic acid sequences but also between two amino acid sequences and between a nucleic acid sequence and an amino acid sequence. Here, the preferred default parameters for the program GAP include: (1) GCG implementation of a unary comparison matrix (containing a value of 1 for identities and 0 for non-identities) for nucleotides, and the weighted amino acid comparison matrix of Gribskov and Burgess, Nucl. Acids Res. 14: 6745, 1986, as described by Schwartz and Dayhoff, eds., Atlas of Polypeptide Sequence and Structure, National Biomedical Research Foundation, pp. 353-358, 1979, or other applicable comparison matrices; (2) a penalty of 30 for each amino acid gap and an additional 1 penalty for each symbol in each gap, or a penalty of 50 for each gap in a nucleotide sequence and an additional 3 penalty for each symbol in each gap; (3) no penalty for end gaps; and (4) no maximum penalty for long gaps. Other sequence comparison programs that are used by skilled artisans and which may be used in the present invention include the BLAST program, version 2.2.7, that can be downloaded from the website of the US National Library of Medicine (http://www.ncbi.nlm.nih.gov/blast/bl2seq/bls.html), or the UW-BLAST 2.0 algorithm. Settings of standard default parameters for UW-BLAST 2.0 are described at the following website: http://blast.wustl.edu. In addition, the BLAST algorithm uses the amino acid scoring matrix BLOSUM 62 and the selection parameters that can be used are as follows: (A) inclusion of a filter for masking segments of query sequence having low compositional complexity (as determined by the SEG program of Wootton and Federhen (Computers and Chemistry, 1993); see also Wootton and Federhen, "Analysis of compositionally biased regions in sequence databases" in Methods Enzymol., 266: 544-71, 1996,) or for masking segments comprising internal repeats of short periodicity (as determined by the XNU program of Claverie and States (Computers and Chemistry, 1993)); and (B) expected probabilities of a match that is to be found merely by chance in accordance with a statistic model of thresholds, or E-scores (Karlin and Altschul, 1990), of statistically significant differences for reporting a match with database sequences (if a statistically significant difference due to a certain match is greater than an E-score threshold, the match is not reported); the numerical value of a preferred E-score threshold is either 0.5 or, in increasing order of preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The variant or mutant of TM2 may also be a protein that is encoded by a nucleic acid comprising a nucleotide sequence that hybridizes with a strand complementary to the nucleotide sequence of SEQ ID NO:1 under stringent conditions and which has the same biotin-binding activity as TM2 has.

The phrase "under stringent conditions" as used herein means hybridizing under conditions of moderate or high stringency. Specifically, conditions of moderate stringency can be readily determined by those having ordinary skill in the art based on, for example, the length of DNA. The basic conditions are set forth in Sambrook et al. Molecular Cloning: A Laboratory Manual, 3rd ed. Chapter 6, Cold Spring Harbor Laboratory Press, 2001, and include use of: a pre-washing solution of 5×SSC, 0.5% SDS, and 1.0 mM EDTA (pH 8.0); hybridizing conditions of about 50% formamide, 2×SSC-6× SSC, preferably 5-6×SSC and 0.5% SDS, at about 42° C. (or other similar hybridization solutions, such as Stark's solution in about 50% formamide at about 42° C.); and washing conditions of about 50-68° C., 0.1-6×SSC, and 0.1% SDS. Preferably, conditions of moderate stringency include hybridizing conditions (and washing conditions) of about 50° C., 6×SSC, and 0.5% SDS. Conditions of high stringency can also be readily determined by the skilled artisan based on, for example, the length of DNA.

Generally, such conditions include hybridization at higher temperatures and/or at lower salt concentrations than the conditions of moderate stringency (e.g., hybridization in the presence of about 0.5% SDS at about 65° C. with 6×SSC to 0.2×SSC, preferably 6×SSC, more preferably 2×SSC, even more preferably 0.2×SSC, or 0.1×SSC) and/or washing, and may be defined as hybridizing conditions of the type described above, and involving washing at approximately 65-68° C. in 0.2-0.1×SSC and 0.1% SDS. In the buffer solution for use in hybridization and washing, SSC (1×SSC consists of 0.15 M NaCl and 15 mM sodium citrate) may be replaced by SSPE (1×SSPE consists of 0.15 M NaCl, 10 mM $NaH_2PO_4$, and 1.25 mM EDTA; pH 7.4), and washing is performed for approximately 15 minutes to one hour after hybridization is complete.

If desired, a commercial hybridization kit may be employed that does not use a radioactive substance as the probe. A specific example is hybridization that employs an ECL direct labeling & detection system (product of Amersham). Stringent hybridization may be performed at 42° C. for 4 hours after a blocking reagent and NaCl are added in respective amounts of 5% (w/v) and 0.5 M to the hybridization buffer in the kit; washing may be performed twice in 0.4% SDS and 0.5×SSC for 20 minutes each at 55° C., then once in 2×SSC for 5 minutes at room temperature.

The biotin-binding activity of the variants or mutants of TM2 can be measured by any one of the known techniques. For example, it may be determined by a fluorescent biotin-based method as described in Kada et al. (Biochim. Biophys. Acta., 1427: 33-43 (1999)). This method is an assay system that makes use of such a nature of fluorescent biotin that if it binds to a biotin-binding site in a biotin-bound protein, its fluorescence intensity becomes extinct. Alternatively, the biotin-binding activity of variant or mutant proteins can also be evaluated using a sensor capable of measuring the protein-biotin binding, such as a biosensor operating on the principle of surface plasmon resonance.

In the modified tamavidin according to the present invention, amino acid residues, desirably not to be modified, will be described below.

Modified Tamavidin in which Non-Specific Binding is Reduced According to the Present Invention The modified TM2 of the present invention comprises an amino acid sequence represented by SEQ ID NO: 2, an amino acid sequence having one to several amino acid mutations in the sequence represented by SEQ ID NO: 2, or an amino acid sequence having 80% or more identity to the sequence represented by SEQ ID NO: 2, and having biotin-binding activity, and is characterized in that the modified TM2 is a protein (the wild type TM2 and variant-type TM2) in which one or more residue(s) selected from the group consisting of:

1) an arginine residue at position 104 of SEQ ID NO: 2;
2) a lysine residue at position 141 of SEQ ID NO: 2;
3) a lysine residue at position 26 of SEQ ID NO: 2; and
4) a lysine residue at position 73 of SEQ ID NO: 2 is replaced with an acidic amino acid residue or a neutral amino acid residue.

The isoelectric point (pI) of the wild type TM2 calculated from its primary structure is about 7.4 whereas the actually measured value is about 8.2 to 8.6. Thus, the wild type TM2 is a neutral to weakly basic protein. The degree of non-specific binding of TM2 is much less than that of avidin and is approximately equal to that of streptavidin, which is a neutral protein.

The present inventors have studied for further reducing non-specific binding of TM2. That is, experiments using TM2 in which a basic amino acid residue is modified to an acidic or neutral amino acid were conducted based on an expectation that, even in a neutral to weakly basic protein, such as TM2, the non-specific binding can be further reduced by decreasing its pI.

It is known that the biotin-binding affinity of streptavidin or avidin is decreased by substitution of one or several amino acids in some cases. Accordingly, in the experiments, modification of amino acid residues was performed, while examination described below was conducted so as not only to reduce the isoelectric point but also not to impair the excellent characteristics, i.e., the high biotin-binding ability, of TM2.

As a result of intensive studies, the present inventors have found that a modified TM2 protein having mutations of one or more residues selected from the group consisting of:

1) an arginine residue (R104) at position 104 of SEQ ID NO: 2;
2) a lysine residue (K141) at position 141 of SEQ ID NO: 2;
3) a lysine residue (K26) at position 26 of SEQ ID NO: 2; and
4) a lysine residue (K73) at position 73 of SEQ ID NO: 2 satisfies the above-described requirements as a modified-type TM2 having a low pI of the present invention. Thus, the present invention has been accomplished.

The amino acid after mutation is an acidic amino acid residue (aspartic acid or glutamic acid) or a neutral amino acid residue (asparagine, serine, glutamine, threonine, glycine, tyrosine, tryptophan, cysteine, methionine, proline, phenylalanine, alanine, valine, leucine, or isoleucine).

In addition, since a nonpolar amino acid could lead to non-specific binding due to hydrophobic interaction, the acidic or neutral amino acid residue preferably has a hydropathy index of 2 or less. The hydropathy index quantifies the degree of hydropathy of each amino acid residue, which is described by, for example, Kyte and Doolittle, J. Mol. Biol., 157, 105-132 (1982), and is well known to those skilled in the art. "The acidic amino acid residues or the neutral amino acid residues having a hydropathy index of 2 or less" are aspartic acid and glutamic acid, which are the acidic amino acid residues, or asparagine, serine, glutamine, threonine, glycine, tyrosine, tryptophan, methionine, proline, and alanine, which are the neutral amino acid residues.

More preferably, 1) the arginine residue at position 104 of SEQ ID NO: 2 and/or 2) the lysine residue at position 141 of SEQ ID NO: 2 is replaced with an acidic amino acid residue or a neutral amino acid residue. More preferably, 1) the arginine residue at position 104 of SEQ ID NO: 2 and/or 2) the lysine residue at position 141 of SEQ ID NO: 2 is replaced with an acidic amino acid residue.

K26 is preferably replaced with A (alanine), K73 is preferably replaced with Q (glutamine), R104 is preferably replaced with E (glutamic acid) or D (aspartic acid), and K141 is preferably replaced with E (glutamic acid) or D (aspartic acid); and R104 is more preferably replaced with E, and K141 is more preferably replaced with E.

The modified TM2 having a low pI of the present invention has an isoelectric point that is significantly lower than that of the wild type TM2. Specifically, Paragraph 1-8) of Example 1 reveals that isoelectric point of every modified TM2 having mutation decreases by 1 or more compared to that of the wild type TM2.

The results elucidate that the modified TM2 protein of the present invention shows lower non-specific binding to nucleic acids and/or proteins than the wild type or mutant-type TM2 protein does. Specifically, Paragraph 1-11) of Example 1 shows a reduction in non-specific binding to DNA. Furthermore, paragraph 1-9) of Example 1 shows a reduction in non-specific adsorption of serum protein. Non-specific binding and adsorption are each reduced to about 60% of that of the wild type TM2 by mutating K26, K73, or K141. In R104-K141 (both R104 and K141 were mutated), non-specific binding and adsorption were each reduced to a level close to 20% of that of TM2. In contrast, although a reduction in non-specific binding to DNAs or cells in a basic amino acid mutant of avidin has been reported (Marttila, et al., (2000) FEBS, 467, pp. 31-36), such a great reduction in non-specific binding of serum protein has not been reported.

Investigation of binding of the modified TM2 having a low pI of the present invention to fibronectin revealed a great reduction in the binding to fibronectin. Fibronectin is a cell adhesion molecule present in extracellular matrix and causes background noise, particularly, in detection of protein in plasma or serum. Thus, less binding to fibronectin is preferred. As shown in Paragraph 1-10) of Example 1, the binding level of fibronectin decreased in all the mutants compared to TM2. In particular, the amounts of fibronectin binding to K141 and R104-K141 are each significantly reduced to 10 to 20% of the amount in the wild type TM2. No relationship between the pI value and the fibronectin-binding ability has been known, and, actually, no clear correlation was observed between the pI value and the degree of reduction in fibronectin binding. In this regard, the reduction in the amounts of fibronectin binding to the K141 and R104-K141 mutants are unpredictably very large.

In one preferred modified TM2 of the present invention of which fibronectin binding is reduced, lysine at position 141 in the TM2 amino acid sequence is modified to an acidic amino acid or a neutral amino acid, more preferably modified to an acidic amino acid or neutral amino acid having a hydropathy index of 2 or less, more preferably modified to E (glutamic acid) or D (aspartic acid), and most preferably to E.

Alternatively, in another modified TM2 of which fibronectin-binding is reduced, R104 and K141 are each modified to an acidic amino acid or a neutral amino acid, more preferably each modified to an acidic amino acid or neutral amino acid having a hydropathy index of 2 or less, more preferably modified to E (glutamic acid) or D (aspartic acid), and most preferably to E.

Modified Tamavidin Having Improved Biotin-Binding Ability

TM2 very tightly binds to biotin with a binding rate constant (ka) of $9.19 \times 10^5$ ($M^{-1}$ $s^{-1}$), a dissociation rate constant (kd) of $6.83 \times 10^{-6}$ ($s^{-1}$), and a dissociation constant (KD) of $7.43 \times 10^{-12}$ (M). The ka, kd, and KD of streptavidin, another biotin-binding protein, similarly measured were respectively 2.28×10$^6$ (M$^{-1}$ s$^{-1}$), 2.52×10$^{-6}$ (s$^{-1}$), and 1.11×10$^{-12}$ (M). That is, the binding strength of TM2 to biotin is of the same order as that of streptavidin, but is slightly lower than that of streptavidin (WO2008/081938 A1). In order to bind a biotin-binding protein to biotin more quickly or in a larger amount, higher biotin-binding ability is desirable.

The present inventors have successfully produced high-affinity modified TM2 having further improved biotin-binding ability by modifying amino acid residues of the wild type TM2 having high original biotin-binding ability. In the high-affinity TM2 of the present invention, at least aspartic acid residue (D40) at position 40 in the amino acid sequence of SEQ ID NO: 2 representing TM2 has been modified. The amino acid after mutation is preferably N (asparagine).

The modification of D40 may be performed in combination with modification of R104, K141, K26, and/or K73 for reducing the above-described non-specific binding (mode 6), or may be performed alone (mode 11). As shown in Examples 2 and 3, modified TM2 in which D40 is modified has biotin-binding ability significantly higher than that of the wild type TM2.

Modified Tamavidin Having Reduced Non-Specific Binding and Improved Biotin-Binding Ability A modified tamavidin produced by combining amino acid mutations of the above-described "modified tamavidin decreased in non-specific binding" and "modified tamavidin increased in biotin-binding ability" showed reduced non-specific binding, and thus enhanced biotin-binding ability. The thus-produced modified tamavidin contains mutation of at least one amino acid residue of K26, K73, R104, and K141 in the amino acid sequence of TM2, and further contains mutation of the amino acid residue of D40 by mutated to N (mode 6).

The amino acid after the mutation of K26, K73, R104, and/or K141 is an acidic or neutral amino acid, preferably, an acidic or neutral amino acid having a hydropathy index of 2 or less (Kyte and Doolittle, J. Mol. Biol., 157, 105-132 (1982)). More preferably, K26 is mutated to A (alanine), K73 is mutated to Q (glutamine), R104 is mutated to E (glutamic acid) or D (aspartic acid), and K141 is mutated to E (glutamic acid) or D (aspartic acid); and more preferably, R104 is mutated to E, and K141 is mutated to E.

In modified tamavidin in which both R104 and D40 were modified, an increase in affinity and a reduction in non-specific binding to protein were observed (in Paragraphs 3-7 and 3-9) of Example 3).

Modified tamavidin in which all R104, K141, and D40 were modified showed a reduction in isoelectric point, an increase in affinity, a reduction in non-specific binding to proteins, a reduction in fibronectin-binding activity, and a reduction in non-specific binding to nucleic acids (in paragraphs 3-6), 3-7), 3-9), 3-10), and 3-11) of Example 3). Furthermore, surprisingly, the heat stability of the protein structure was notably improved (in paragraph 3-8) of Example 3).

Accordingly, it is preferred to modify both D40 and R104 amino acid residues, and more preferred to modify all D40, R104, and K141 residues.

As described above, the modified TM2 of the present invention is preferably, but is not limited to, selected from the group consisting of:

a modified biotin-binding protein (D40N-R104E) in which the aspartic acid residue at position 40 in SEQ ID NO: 2 is replaced with an asparagine residue, and the arginine residue at position 104 is replaced with a glutamic acid residue;

a modified biotin-binding protein (D40N-K141E) in which the aspartic acid residue at position 40 in SEQ ID NO: 2 is replaced with an asparagine residue, and the lysine residue at position 141 is replaced with a glutamic acid residue; and a modified biotin-binding protein (D40N-R104E-K141E) in which the aspartic acid residue at position 40 in SEQ ID NO: 2 is replaced with an asparagine residue, the arginine residue at position 104 is replaced with a glutamic acid residue, and the lysine residue at position 141 is replaced with a glutamic acid residue.

In a preferred embodiment, the modified TM2 protein of the present invention comprises, for example, any of the amino acid sequences SEQ ID NOs: 8, 10, 16, 20, 22, 24, and 25.

More preferred are D40N-R104E, D40N-K141E, and D40N-R104E-K141E, and most preferred is D40N-R104E-K141E.

The modified TM2 protein of the present invention satisfies at least one property selected from the following properties i) to iv):

i) having an isoelectric point lower than that of a protein consisting of an amino acid sequence represented by SEQ ID NO: 2;

ii) to show less non-specific binding to nucleic acids and/or proteins compared to a protein consisting of an amino acid sequence represented by SEQ ID NO: 2;

iii) to show less fibronectin-binding activity compared to a protein consisting of an amino acid sequence represented by SEQ ID NO: 2; and iv) to show more biotin-binding activity compared to a protein consisting of an amino acid sequence represented by SEQ ID NO: 2.

Regarding the property i), since the isoelectric point of the wild type TM2 is about 8.5 to 8.8, the isoelectric point of the modified TM2 of the present invention is preferably 8.0 or less and more preferably 7.7 or less.

Regarding the property iii), when the fibronectin-binding property of the wild type TM2 is defined to 1.3 to 1.4, the fibronectin-binding activity of the modified TM2 of the present invention is preferably 1.0 or less, more preferably 0.7 or less, 0.25 or less, or 0.15 or less.

Amino Acid Residue that is Desirably not Modified in the Modified TM2 of the Present Invention The modification of amino acid residues in the modified TM2 of the present invention should not affect the biotin-binding ability. Incidentally, the biotin pocket of streptavidin, one biotin-binding protein, has been already revealed to some extent. The amino acid homology between the streptavidin and TM2 is only about 50%. The present inventors have compared the amino acid sequences of TM2 and streptavidin in order to find information on biotin pocket of TM2. As a result, it has been found that among the amino acids forming the biotin pocket of streptavidin, residues directly interacting with biotin, i.e., N23, S27, Y43, S45, N49, W79, S88, T90, W92, W108, W120, and D128 (Weber, et al., (1989) Science 243: 85-88, Livnah, et al., (1993) Proc. Natl. Acad. Sci. U.S.A. 90: 5076-5080) correspond to N14, S18, Y34, S36, D40, W69, S76, T78, W80, W96, W108, and D116, respectively, of TM2 and that the biotin pocket is well preserved.

The only difference was that N (asparagine) at position 49 of streptavidin is, in TM2, D (aspartic acid) at position 40, and the biotin-binding ability of TM2 D40N in which the aspartic acid was modified to asparagine, as in streptavidin, was increased as described above. These results suggest that the biotin-binding pockets of TM2 and streptavidin have very similar structures and that these amino acid residues highly involve binding to biotin.

In particular, since four tryptophan residues (W69, W80, W96, and W108) are believed to play very important parts in the structure of the biotin pocket, it is preferred that they be not modified. At the same time, other amino acids that are believed to involve binding to biotin, that is, in TM2, it is also preferred that the amino acid residues (N14, S18, Y34, S36, S76, T78, and D116) believed to directly interact with biotin be not be modified. Alternatively, in the case where these residues are modified, it is preferred that the amino acids be modified to amino acids having similar properties and structures so that the biotin-binding ability is retained. For example, asparagine (N14) is desirably modified to glutamine (Q) or aspartic acid (D) and preferably aspartic acid; aspartic acid (D40) is desirably modified to asparagine (N); serine (S18, S36, and S76) is modified to threonine (T) or tyrosine (Y) and preferably threonine; tyrosine (Y34) is desirably modified to serine (S), threonine (T), or phenylalanine (F) and preferably phenylalanine; threonine (T78) is desirably modified to serine (S) or tyrosine (Y) and preferably serine; and aspartic acid (D116) is desirably modified to glutamic acid (E) or asparagine (N) and preferably asparagine.

Method of modification of amino acid

The modified TM2 of the present invention can be obtained by modifying an amino acid or amino acids of TM2 by any known method that causes mutation in an amino acid sequence without any limitation. Preferably, modification is achieved by obtaining a nucleotide sequence of the nucleic acid encoding TM2.

For example, in order to modify the amino acid at a specific position of an amino acid sequence, a method utilizing PCR can be employed (Higuchi, et al., (1988), Ho, et al., (1989)). That is, PCR is conducted using a primer containing a mismatch codon for a target mutation to produce DNA encoding an objective mutant, and to allow the DNA to express the objective mutant.

The variants or mutants due to amino acid deletions, substitutions, insertions and/or additions can be prepared from the native protein encoding DNA by applying a well-known technique, say, site-specific mutagenesis (see, for example, Nucleic Acid Research, Vol. 10, No. 20, p. 6487-6500, 1982, which is incorporated herein by reference in its entirety). Site-specific mutagenesis may be performed as follows using synthetic oligonucleotide primers that are complementary to the single-stranded phage DNA to be mutated, except for a specific mismatch that corresponds to the desirable mutation. To be more specific, the above-mentioned synthetic oligonucleotides are used as primers to synthesize a strand complementary to the phage and a host cell is transformed with the resulting double-stranded DNA. A culture of the transformed cell is plated on agar and plaques are formed from the phage-containing single cells. Then, theoretically, 50% of the new colonies contain phages having a mutation in a single strand and the remaining 50% have the original sequence. The obtained plaques are hybridized with a synthetic probe, as labeled by kinase treatment, at a temperature that allows for hybridization with those colonies that exhibit complete match with DNA having the above-mentioned desirable mutation but that does not allow for hybridization with those colonies having the original strand. Subsequently, plaques that hybridize with that probe are picked and cultured for DNA recovery.

Nucleic Acid Encoding Modified Tamavidin 2 (TM2) Protein

The present invention provides a nucleic acid encoding the modified TM2 of the present invention. The nucleic acid includes, for example, a nucleotide sequence obtained by modifying the nucleotide sequence (SEQ ID NO: 1) of TM2 to the nucleotide sequence encoding the modified TM2 protein having a modified amino acid or modified amino acids. The nucleotide sequence to be modified is not limited as long as the nucleotide sequence after modification encodes the modified amino acid or modified amino acids. Examples thereof include a nucleic acid having a nucleotide sequence modified for providing the modification of the present invention to the nucleic acid consisting of the nucleotide sequence of SEQ ID NO: 1 or a nucleic acid which hybridizes to a complementary strand of the nucleic acid consisting of the nucleotide sequence of SEQ ID NO: 1 under stringent conditions and encodes a protein having biotin-binding activity (hereinafter referred to as "TM2 gene").

The nucleic acid of the present invention preferably encodes an amino acid sequence: SEQ ID NO: 8, 10, 16, 20, 22, 24, or 25, and more preferably encodes an amino acid sequence SEQ ID NO: 22 or 24. The nucleic acid of the present invention preferably consists of a nucleic acid sequence: SEQ ID NO: 7, 9, 15, 19, 21, or 23, and more preferably consists of a nucleic acid sequence SEQ ID NO: 21 or 23.

Vector Containing Nucleic Acid of the Present Invention

The present invention provides a vector containing a nucleic acid encoding the modified TM2 protein. The vector is an expression vector for expressing a modified TM2 protein.

The nucleic acid encoding a modified TM2 protein of the present invention is as described in the "Nucleic acid encoding modified tamavidin 2 protein" and is not particularly limited.

The vector may have a restriction enzyme recognition site or a sequence used in a Gateway system (Invitrogen), such as aatB1, aatB2, or aatB3, on one end or both ends of the nucleic acid encoding a modified TM2 protein. Furthermore, a promoter and a terminator that function in desired host cells may be located upstream and downstream, respectively, of the nucleic acid encoding a modified TM2 protein.

The type of the restriction enzyme recognition site is not particularly limited, but the expression vector preferably has only one type of recognition site. The number of recognition sites is not particularly limited, but is one or more and preferably 10 or more.

Furthermore, a nucleic acid sequence, encoding a linker amino acid sequence (which is not particularly limited, and may be usually used by those skilled in the art, for example, a sequence containing a large number of glycines and serines) composed of at least one amino acid, preferably at least five amino acids, more preferably at least ten amino acids, more preferably at least 25 amino acids, and at most 50 amino acids, may be located between the restriction enzyme recognition site and the modified TM2 nucleic acid or between the aatB sequence and the modified TM2 nucleic acid. In addition, for example, sequences encoding recognition sites for enterokinase or protease, such as Factor Xa, may be located although it is not particularly limited.

For example, in the case that a gene encoding an antibody such as scFv or Fab is inserted into the present expression vector, under reductive conditions not suitable for expression of a fusion protein, such as the inside of cytoplasm, a nucleic acid sequence encoding a leader peptide, such as a signal peptide or a secretory signal, may be located between the promoter and the unit including a sequence for inserting a nucleic acid encoding the modified tamavidin.

The vector of the present invention is preferably an expression vector. In addition to such an expression unit, the expression vector may include a unit for enabling replication in desired host cells, for example, a replication origin or a drug resistance marker gene for selecting desired host cells. The host cell is not particularly limited, but is preferably *Escheri-* chia coli. In addition, an appropriate expression control system such as a lactose repressor system in Escherichia coli may be incorporated.

Carrier for Immobilizing Modified Tamavidin

The present invention provides a carrier for immobilizing the modified TM2 protein of the present invention.

The material constituting the carrier may be a known one, and examples thereof include, but are not limited to, cellulose, Teflon, nitrocellulose, agarose, dextran, chitosan, polystyrene, polyacrylamide, polyester, polycarbonate, polyamide, polypropylene, nylon, polydivinylidene difluoride, latex, silica, glass, glass fiber, gold, platinum, silver, copper, iron, stainless steel, ferrite, silicon wafer, polyethylene, polyethyleneimine, polylactic acid, resins, polysaccharides, proteins (e.g., albumin), carbon, and combinations thereof. A preferred carrier has a certain level of strength and stable composition and is low in non-specific binding.

The solid carrier may have any shape including, but not limited to, beads, magnetic beads, thin films, microtubes, filters, plates, microplates, carbon nanotubes, and sensor chips. Flat solid carriers such as thin films and plates may be provided with pits, channels, filter bottoms, or the like as known in the art.

In an embodiment of the present invention, the beads may have a spherical diameter in the range of about 25 nm to about 1 mm. In a preferred embodiment, the beads may have a diameter in the range of about 50 nm to about 10 µm. The size of the beads may be selected depending on the intended purpose. Since some bacterial spores have a size of an order of about 1 µm, preferred beads for capturing such spores have a diameter larger than 1 µm.

The immobilization of a protein to the carrier is not particularly limited and may be performed by a known method for binding a protein to a carrier. Specifically, the method is appropriately selected by those skilled in the art depending on the type of the carrier, and so on.

Advantageous Effects of Invention

According to the present invention, a modified tamavidin improved in properties, such as a reduction in non-specific binding and/or a further improvement in biotin-binding, while retaining the characteristics of tamavidin, i.e., high biotin-binding ability is provided. The use of the modified tamavidin in detection, for example, in immunoassay or nucleic acid hybridization assay, for measuring an analyte utilizing avidin-biotin binding can reduce background, increase sensitivity, and maintain the binding property with biotin in severe conditions (e.g., at high temperature in the presence of a denaturation agent and an enzyme).

EXAMPLES

Figure 1:
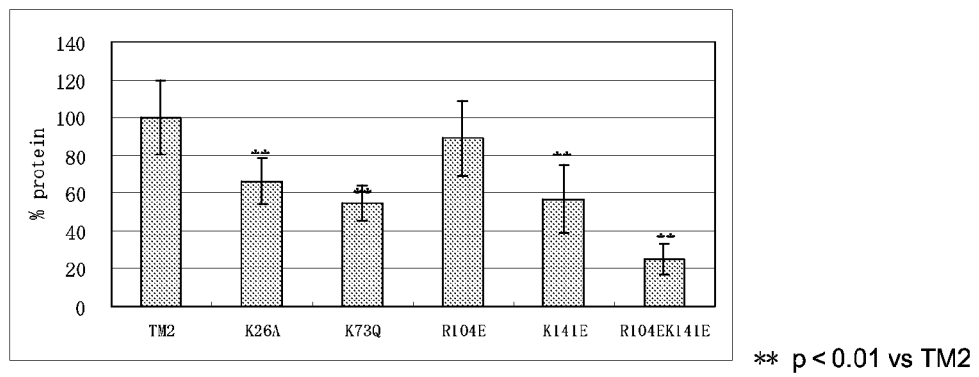
FIG. 1 shows non-specific binding of low-pI modified TM2 proteins of the present invention to serum protein-immobilizing magnetic beads (** $p<0.01$ vs TM2).
Figure 2:
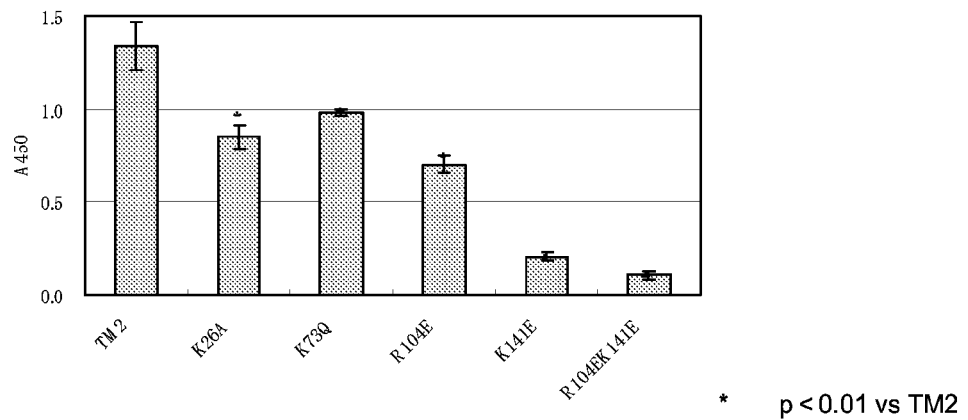
FIG. 2 shows non-specific binding of low-pI modified TM2 proteins of the present invention to fibronectin (* $p<0.01$ vs TM2).

The present invention will be specifically described with reference to the following examples, but the examples are not intended to limit the technical scope of the present invention. Those skilled in the art can readily add modifications/changes to the present invention on the basis of the description herein, and such modifications/changes are included in the technical scope of the present invention.

Example 1

Construction and Analysis of Low-pI TM2

1-1) Construction of Low-pI TM2

In order to reduce the isoelectric point of TM2, a basic amino acid residue in TM2 was replaced with a neutral amino acid or an acidic amino acid to construct the following seven mutants.

(1) a TM2 mutant in which lysine at position 26 was replaced with alanine (hereinafter referred to as "TM2 K26A"; its nucleotide sequence is listed in SEQ ID NO: 3 and the amino acid sequence in SEQ ID NO: 4);

(2) a TM2 mutant in which lysine at position 73 was replaced with glutamine (hereinafter referred to as "TM2 K73Q"; its nucleotide sequence is listed in SEQ ID NO: 5, and the amino acid sequence in SEQ ID NO: 6);

(3) a TM2 mutant in which arginine at position 104 was replaced with glutamic acid (hereinafter referred to as "TM2 R104E; its nucleotide sequence is listed in SEQ ID NO: 7, and the amino acid sequence in SEQ ID NO: 8);

(4) a TM2 mutant in which lysine at position 141 was replaced with glutamic acid (hereinafter referred to as "TM2 K141E; its nucleotide sequence is listed in SEQ ID NO: 9, and the amino acid sequence in SEQ ID NO: 10);

(5) a TM2 mutant in which lysine at position 33 was replaced with threonine, and lysine at position 37 was replaced with alanine (hereinafter referred to as "TM2 K33TK37A"; its nucleotide sequence is listed in SEQ ID NO: 11, and the amino acid sequence in SEQ ID NO: 12);

(6) a TM2 mutant in which lysine at position 33 was replaced with threonine, lysine at position 37 was replaced with alanine, and arginine at position 104 was replaced with glutamic acid (hereinafter referred to as "TM2 K33TK37AR104E"; its nucleotide sequence is listed in SEQ ID NO: 13, and the amino acid sequence in SEQ ID NO: 14); and (7) a TM2 mutant in which arginine at position 104 was replaced with glutamic acid, and lysine at position 141 was replaced with glutamic acid (hereinafter referred to as "TM2 R104EK141E"; its nucleotide sequence is listed in SEQ ID NO: 15, and the amino acid sequence in SEQ ID NO: 16).

(8) a TM2 mutant in which lysine at position 19 is replaced with threonine (hereinafter referred to as "TM2 K19T", its nucleotide sequence is listed in SEQ ID NO: 17, and the amino acid sequence in SEQ ID NO: 18);

E of R104E, and T and A of K33TK37A were determined through comparison of amino acid sequences of TM2 and streptavidin with reference to the amino acids at the corresponding sites on the streptavidin sequence. E of K141E was determined with reference to the amino acid at the corresponding site on the tamavidin 1 sequence.

First, in order to construct low-pI TM2, primers for introducing each mutation were designed: A Tm2NtermPci primer composed of the 5'-site of the TM2 gene and a sequence encoding PciI restriction enzyme cleavage site (ACATGT) located upstream of the 5'-site, a Tm2CtermBam primer composed of the 3'-site of the TM2 gene and a sequence encoding BamHI restriction enzyme cleavage site (GGATCC) located downstream of the 3'-site was designed, and a series of sense primers containing mismatch codons for each mutant, and their antisense primers are as follows (SEQ ID NOs: 26 to 37):

TABLE 1

Primers for constructing low-pI TM2

| Name Sequence (5'-3') | Length |
|---|---|
| Tm2NtermPci<br>AAA ACA TGT CAG ACG TTC AAT CTT C | 25 mer |
| Tm2CtermBam<br>TTT GGA TCC TTA CTT CAA CCT CGG TGC G | 28 mer |
| Tm2 K26A PciIFW<br>TTT TTT ACA TGT CAG ACG TTC AAT CTT CAC TCA<br>CCG GAA CCT GGT ACA ATG AAC TCA ACT CCA AGA<br>TGG AAT TGA CTG CAA ACG CAG ACG GTA CTC TCA<br>CTG GAA AGT | 108 mer |
| Tm2 K73Q F<br>TCC TGG GAG AAC AGT CAAATT CAT TCC GCT ACG | 33 mer |
| Tm2 K73Q R<br>TCC TGG GAG AAC AGT CAAATT CAT TCC GCT ACG | 33 mer |
| Tm2 K33,37TA F<br>ACT CTC ACT GGA ACG TAC CTC TCC GCA GTT<br>GGG GAT GTC | 39 mer |
| Tm2 K33,37TA R<br>GAC ATC CCC AAC TGC GGA GAG GTA CGT TCC<br>AGT GAG AGT | 39 mer |
| Tm2 R104E F<br>TCG AGC ACT GCG GAA GGG GAC GTA TGG | 27 mer |
| Tm2 R104E R<br>CCA TAC GTC CCC TTC CGC AGT GCT CGA | 27 mer |
| Tm2 K141E Bam<br>TTT GGA TCC TTA CTC CAA CCT CGG TGC GCG | 30 mer |
| Tm2 K19T F<br>GAA CTC AAC TCC ACG ATG GAA TTG ACT | 27 mer |
| Tm2 K19T R<br>AGT CAA TTC CAT CGT GGA GTT GAG TTC | 27 mer |

From the top, SEQ ID NOs: 26 to 37
The restriction enzyme recognition sites are underlined, and mutation sites are shown by dotted lines.

1-2) PCR

In order to construct a low-pI TM2 gene, two-stage PCR was performed. In the first-stage PCR, using a plasmid of a pTrc99A vector containing a TM2 gene as a template, the 5'-site was amplified using primer Tm2NtermPci and an antisense primer, Tm2 K26A R, Tm2 K73Q R, Tm2 K33TK37A R, Tm2 R104E R, or Tm2 K19T R, containing a mismatch codon of each mutant, and the 3'-site was amplified using primer Tm2CtermBam and a sense primer, Tm2 K26A F, Tm2 K73Q F, Tm2 K33TK37A F, Tm2 R104E F, or Tm2 K19T F, containing a mismatch codon of each mutant.

In terms of TM2 K141E, mutation was introduced into single PCR reaction using primers Tm2NtermPci and Tm2 K141E Bam.

The PCR was conducted under the reaction conditions: 50 µL of a reaction solution containing a template DNA (500 ng), 10× Pyrobest buffer (Takara, 5 µL), 2.5 mM dNTP (4 µL), primers (25 pmoles, each), and 5 U/µL Pyrobest DNA polymerase (Takara, 0.5 µL), and started with 3 min at 96° C. followed by ten cycles of 1 min at 96° C., 1 min at 55° C., and 2 min at 72° C., and ended with 6 min at 72° C. in a program temperature control system PC-700 (ASTEK). As a result, PCR products, that is, about 120 bp of TM2 K33TK37A and about 330 bp of TM2 K R104E were produced in the 5'-site, and about 310 bp of TM2 K33TK37A, about 100 bp of TM2 K R104E, and about 60 bp of TM2 K19T were produced in the 3'-site. In terms of TM2 K141E, 430 bp of a PCR product was obtained.

These PCR products were subjected to agarose electrophoresis using low-melting-point agarose (SeaPlaqueGTG) in a TAE buffer. Each DNA fragment was cut out together with the gel, and the same amount of 200 mM NaCl as the gel was added thereto, followed by treatment at 70° C. for 10 min to melt the gel. This sample was subjected to phenol extraction, phenol/chloroform extraction, and chloroform extraction each once, and the 5'-site and 3'-site DNA fragments were collected by ethanol precipitation. Using these fragments as templates, the second-stage PCR was conducted for constructing genes other than TM2 K141E using primers Tm2NtermPci and Tm2CtermBam. The reaction conditions were the same as those of the first-stage PCR. As a result, 430 bp of each PCR product was obtained.

1-3) Cloning

The low-pI TM2 gene fragments obtained by PCR were cloned into a pCR4 Blunt TOPO vector (Invitrogen). The ligation reaction was conducted in accordance with the instruction attached to the vector kit. The DNA was introduced into *Escherichia coli* TB1 by electroporation, and the plasmid DNA was extracted in accordance with a common process (Sambrook, et al., 1989, Molecular Cloning, A laboratory manual, $2^{nd}$ edition). The nucleotide sequences of PCR products of the clones that were confirmed the insertion were determined from both ends using an M13 primer (Takara) with an ABI PRISM fluorescence sequencer (Model 310 Genetic Analyzer, Perkin Elmer) to confirm modification of the target nucleotide.

The plasmid, wherein the gene (the nucleotide sequence thereof has been confirmed) was introduced into CR4 Blupnt TOPO, was double-digested with PciI and BamHI, and a DNA fragment was collected by gel purification in accordance with the above-described method. The fragment was ligated to expression vector pTrc99A for *Escherichia coli*, which has been digested with NcoI and BamHI in advance, using Ligation kit (Takara). The ligation product was transformed into *Escherichia coli* TB1, and extraction of plasmid DNA and restriction enzyme analysis were performed in accordance with a common process for confirmation of the presence of the inserted gene to obtain low-pI TM2 protein-expressing vectors TM2 K26A/pTrc99A, TM2 K73Q/pTrc99A, TM2 K33TK37A, TM2 R104E/pTrc99A, TM2 K141E/pTrc99A, and TM2 K19T/pTrc99A. Furthermore, a gene encoding TM2 R104EK141E was constructed through introduction of mutation by PCR using vector TM2 R104E/ pTrc99A as a template and using primers Tm2NtermPci and Tm2 K141E Bam. A gene encoding TM2 K33TK37AR104E was constructed through introduction of mutation by PCR using vector TM2 K33TK37A/pTrc99A as a template and using primers Tm2NtermPci and Tm2 K141E Bam and was cloned by the same method described above.

1-4) Expression of Low-pI TM2 in *Escherichia coli*

*Escherichia coli* TB1 transformed with low-pI TM2/pTrc99A was inoculated into an LB culture medium (6 mL) containing an antibiotic, ampicillin (final concentration: 100 μg/mL) and was cultured with shaking at 37° C. until the absorbance at 600 nm, $OD_{600}$, reached 0.5, followed by addition of 1 mM IPTG and further shaking culture at 37° C. overnight. *Escherichia coli* was collected from 1 mL of the culture solution by centrifugation and was suspended in 20 mM phosphate buffer (pH 7, 400 μL), followed by disruption of bacterial cells by sonication. The disruption solution was centrifuged (15000 rpm) to obtain a soluble fraction as the supernatant.

The soluble fraction was subjected to western blotting analysis: the soluble fraction and the same volume of 2×SDS sample buffer (250 mM Tris-HCl, pH 6.8, 20% 2-mercaptoethanol, 20% SDS, 20% glycerol) were mixed and were heated at 95° C. for 10 minutes, followed by separation by SDS-PAGE for western blotting analysis using anti-TM2 rabbit antibody (PCT/JP2006/326260) as the primary antibody and alkaline phosphate-labeled anti-rabbit IgG antibody (BIO-RAD) as the secondary antibody. The results of the western blotting analysis showed that a band near 15.5 kDa was detected in every *Escherichia coli* transformed with low-pI TM2/pTrc99A, but the band was not detected in *Escherichia coli* transformed with a pTrc99A vector not containing the low-pI TM2 gene. The sizes of these bands agreed with the molecular weight, 15.5 kDa, of a monomer predicted from the amino acid sequence of TM2.

The formation of a tetramer of TM2 mutants in the non-denatured state was confirmed in accordance with the method by Bayer, et al., (1996, Electrophoresis, 17(8), 1319-24). That is, an SDS sample buffer not containing a reducing agent, such as DTT or mercaptoethanol, and the soluble fraction of a TM2 mutant were mixed, followed by SDS-PAGE analysis without heat treatment. As a result, a band having the same size as that of the wild type TM2 was detected in every TM2 mutant, which demonstrated the formation of the tetramer. The expression level of a soluble low-pI TM2 protein was 20 mg for 1 L of the culture solution in each of TM2 K26A, TM2 K73Q, TM2 R104E, TM2 K141E, and TM2 R104EK141E. This was equivalent to the expression level of the wild-type TM2.

In contrast, unlike these mutants, the expression levels of TM2K33TK37A, TM2 K33TK37AR104E, and TM2 K19T were each as low as 2 mg.

1-5) Measurement of Activity by Fluorescent Biotin

The biotin-binding ability of each low-pI TM2 expressed in *Escherichia coli* was confirmed in accordance with the method in Biochim. Biophys. Acta, 1427, 44-48 (1999): solutions (each 150 μL) of an assay buffer (50 mM $NaH_2PO_4$, 100 mM NaCl, 1 mM EDTA (pH 7.5)) gradually containing a extract solution extracted from 25 mL of culture solution of each low-pI TM2 with 1.5 mL of 20 mM phosphate buffer (pH 7) were prepared. Each of these solutions and 10 pmol/μL fluorescent biotin solution (biotin-4-fluorescene: Molecular Probe, 50 μL (500 pmol)) were mixed and subjected to reaction at room temperature for 10 minutes, followed by measurement of fluorescent intensity at Ex=460 nm and Em=525 nm using Infinite M200 (TECAN).

The results showed that the fluorescent intensity decreased in proportion to the increase in the amount of the low-pI TM2 extract. This demonstrated that the full-length TM2 mutant in which a basic amino acid of TM2 was replaced with a neutral or acidic amino acid bound to a biotin-like compound.

1-6) Purification of Low-pI TM2

The low-pI TM2 was purified in accordance with the method by Hofmann, et al., (1980) using a column filled with 2-iminobiotin agarose (Sigma). Each *Escherichia coli* culture solution (25 mL) induced to expression of low-pI TM2 was mixed with 50 mM CAPS (pH 11, 15 mL) containing 50 mM NaCl to suspend the cells, followed by ultrasonic disruption. The supernatant was supplied to a column filled with 2-iminobiotin agarose (500 μL). The column was completely washed with 50 mM CAPS (pH 11) containing 500 mM NaCl, followed by elution with 50 mM $NH_4OAC$ (pH 4). The amount of each purified low-pI TM2 protein was approximately the same level as the amount expressed in *Escherichia coli* to show a purity of 95% or more.

1-7) Measurement of Biotin-Binding Ability

A biotin-binding test of low-pI TM2 was conducted using Biacore (registered trademark) 3000 (Biacore, a biosensor utilizing the principle of surface plasmon resonance). Biotinylated bovine serum albumin (BSA) was immobilized on CM5 sensor chips (Biacore) by amine-coupling with EZ-Link (registered trademark) NHS-LC-Biotin (22.4 Å) or EZ-Link (registered trademark) NHS-LCLC-Biotin (30.5 Å) (both are products of PIERCE). HBS-EP (Biacore) was used as a running buffer, and each low-pI TM2 (40 μL) was injected at 25° C. and a flow rate of 20 μL/min for 2 minutes.

From the resulting sensorgrams, the binding rate constant (ka), the dissociation rate constant (kd), and the dissociation constant (KD) were calculated using an analysis software, BIAevaluation version 4.1. Table 2 shows the results. The values shown in parentheses in the table indicate that they are lower than the detection limit ($ka<5\times10^{-6}$) of a Biacore 3000. Every low-pI TM2 exhibits specific binding to biotin and thus demonstrates that the mutation does not significantly affect biotin-binding ability.

TABLE 2

Analysis of interaction between low-pI TM2 and biotin

| Sample Name | ka | kd | KD |
|---|---|---|---|
| BSA-LCLC-Biotin (30.5 Å) | | | |
| TM2 R104E | $5.8 \times 10^{5}$ | $(5.6 \times 10^{-7})$ | $(9.9 \times 10^{-13})$ |
| TM2 K141E | $5.8 \times 10^{5}$ | $(1.1 \times 10^{-6})$ | $(2.0 \times 10^{-12})$ |
| TM2 K33TK37A | $2.5 \times 10^{5}$ | $(7.2 \times 10^{-7})$ | $(2.3 \times 10^{-12})$ |
| TM2 K33TK37AR104E | $6.3 \times 10^{5}$ | $(1.4 \times 10^{-6})$ | $(2.7 \times 10^{-12})$ |
| TM2 | $9.2 \times 10^{5}$ | $6.8 \times 10^{-6}$ | $7.4 \times 10^{-12}$ |
| SA-LC-Biotin (22.4 Å) | | | |
| TM2 K26A | $5.0 \times 10^{5}$ | $(6.5 \times 10^{-7})$ | $(1.7 \times 10^{-12})$ |
| TM2 K73Q | $5.9 \times 10^{5}$ | $(1.7 \times 10^{-6})$ | $(2.8 \times 10^{-12})$ |
| TM2 R104EK141E | $1.2 \times 10^{6}$ | $(5.8 \times 10^{-10})$ | $(5.0 \times 10^{-16})$ |
| TM2 | $9.9 \times 10^{5}$ | $(1.2 \times 10^{-6})$ | $(1.3 \times 10^{-12})$ |

1-8) Isoelectric Focusing Electrophoresis

The isoelectric point of each low-pI TM2 was measured by isoelectric focusing electrophoresis using an XCell SureLock Mini-Cell (Invitrogen). In accordance with the instruction, each low-pI TM2 (500 ng) and an IEF sample buffer (pH 3 to 10 (2×), Invitrogen) were mixed and were added to a polyacrylamide gel (pH 3 to 10, IEF Gel, Invitrogen) at a pH ranging from 3 to 10, followed by electrophoresis at a variable voltage of 100 V for 1 hour, 200 V for 1 hour, and 500 V for 45 minutes in this order.

After the electrophoresis, the gel was shaken in a blotting buffer (0.7% acetic acid) for 10 minutes and then was transferred onto a PVDF membrane at 10 V for 1 hour using an XCell ll Blot Module (Invitrogen). The PVDF membrane was subjected to reaction with anti-TM2 rabbit antibody (PCT/W2006/326260) serving as a primary antibody and with alkaline phosphate-labeled anti-rabbit IgG antibody (BIO-RAD) serving as a secondary antibody, followed by detection of bands with Alkaline Phosphatase Substrate Kit II <VECTOR Black> (VECTRO).

The results revealed that the electric point of every TM2 mutant was lower than that of the wild type TM2 by 1 or more. Table 3 shows the pI values actually measured by isoelectric focusing electrophoresis and the pI values calculated by Genetyx.

TABLE 3

Isoelectric points of low-pI TM2

| Sample Name | pI calculated | pI observed |
|---|---|---|
| TM2 K19T | 6.3 | 6.6 to 7.5 |
| TM2 K26A | 6.3 | 7.3 to 7.6 |
| TM2 K73Q | 6.3 | 7.7 |
| TM2 R104E | 5.9 | 7.0 to 7.5 |
| TM2 K141E | 5.9 | 6.6 to 7.2 |
| TM2 K33TK37A | 5.8 | 6.2 |
| TM2 R104EK141E | 5.1 | 6.2 |
| TM2 K33TK37AR104E | 5.1 | 5.9 to 6.0 |
| TM2 | 7.4 | 8.5 to 8.8 |

1-9) Non-Specific Binding to Human Serum

In this embodiment, non-specific binding to human serum was investigated as non-specific adsorption of low-pI TM2 to serum protein-immobilized magnetic beads. Specifically, in order to investigate the non-specific binding of low-pI TM2, the amount of low-pI TM2 adsorbed to magnetic beads to which human serum protein was covalently bonded was measured. TM2 K26A, TM2 K73Q, TM2 R104E, TM2 K141E, and TM2 R104EK141E, which were highly expressed in *Escherichia coli*, were used as the low-pI TM2 to be investigated.

Human serum protein and magnetic beads were bound to each other as follows. Magnetic beads having surfaces coated with carboxyl groups (Dynabeads M-270 Carboxylic Acid, Dynal, 210 μL) were washed with 0.01 N sodium hydroxide (210 μL) for 10 minutes and then with ultrapure water (210 μL) for 10 minutes three times. To the washed magnetic beads, 1-ethyl-3-(3-dimethylaminopropyl)carbodiimide hydrochloride (EDC, PIERCE) dissolved in cooled ultrapure water was added into a final concentration of 0.2 M, and the mixture was shaken at room temperature for 30 minutes. Then, the magnetic beads were washed with cooled ultrapure water (210 μL) and then with 50 mM MES buffer (pH 5.0, 210 μL).

To the magnetic beads, 1 mg/mL human serum protein (CHEMICON, 210 μL) dialyzed with 50 mM MES buffer (pH 5.0) was added. The mixture was shaken at room temperature for 30 minutes to covalently bind the human serum protein to the magnetic beads. The magnetic beads were collected with a magnet to remove the supernatant. The unreacted active groups on the beads were eliminated with 50 mM tris buffer (pH 7.0, 210 μL), and then the magnetic beads were blocked with a PBS buffer (420 μL) containing 0.5% BSA and 0.1% Tween 20. The magnetic beads were suspended in a PBS buffer (210 μL) to obtain human serum protein-immobilized magnetic beads.

The magnetic beads (7 μL) and 0.56 μg/mL of each low-pI TM2 (100 μL) were mixed for reaction at room temperature for 1 hour. The magnetic beads were collected with a magnetic, and the supernatant was removed. After washing with 20 mM potassium phosphate buffer (500 μL) containing 500 mM sodium chloride, the magnetic beads were mixed with 20 μL of 2×SDS sample buffer (250 mM Tris-HCl, pH 6.8, 20% 2-mercaptoethanol, 20% SDS, 20% glycerol), followed by heating at 95° C. for 20 minutes to dissociate the low-pI TM2 from the magnetic beads.

This sample was subjected to SDS-PAGE and then western blotting analysis to determine the amount of the low-pI TM2. Anti-tamavidin 2 rabbit antibody and alkaline phosphatase-labeled anti-rabbit IgG goat antibody were used as the primary antibody and the secondary antibody, respectively. The bands were detected with Alkaline Phosphatase Substrate Kit II <VECTOR Black> (VECTRO) and were quantified with Las-3000 (FUJIFILM). FIG. 1 shows the results.

As shown in FIG. 1, the adsorption of the low-pI TM2 to human serum protein was decreased compared to the wild type TM2 by 10% in TM2 R104E, by 30% in TM2 K26A, by 40% in K73Q and K141E, and by 70% in TM2 R104EK141E. Thus, the non-specific binding of K26A, K73Q, K141E, and K104EK141E were significantly low compared to that of TM2.

1-10) Non-Specific Binding to Fibronectin

The fibronectin-binding of each low-pI TM2 was compared using a microplate to which fibronectin was immobilized. The concentration of fibronectin was adjusted to 50 μg/mL with a fixation solution exclusive for a New ELISA plate, and the fibronectin solution (50 μL) was added to each New ELISA plate (Sumitomo Bakelite), followed by shaking at 37° C. for 4 hours for immobilization. Then, the plate was washed with 0.1% Triton X-100-containing PBS (300 μL) three times and was then dried naturally.

TM2, K26A, K73Q, R104E, K141E, and R104EK141E mutants (50 μL each) were each added to the corresponding well of the plate and left at room temperature for 1 hour. The plate was washed with 300 μL/well of PBST (PBS buffer containing 0.1% Tween 20) three times. Then, biotinylated HRP diluted 5000 times with PBST containing 0.5% BSA was added at 50 μL/well and allowed to react with the mutant at room temperature for 1 hour. After washing with 300 μL/well of PBST three times, 50 μL/well of 1-Step Ultra TMB-ELISA solution was added to each well for color development. After termination of the color development with 50 μL/well of 2M sulfuric acid, absorbance at 450 nm was measured with an Infinite 200 microplate reader. The results showed that the fibronectin binding was significantly decreased in all low-pI TM2 mutants compared to TM2.

FIG. 2 shows the results. As shown in FIG. 2, the effect on inhibition of binding to fibronectin was high in R104EK141E, K141E, R104E, K26A, and K73Q in this order.

1-11) Non-Specific Binding to DNA

Non-specific binding of low-pI TM2 to DNA was analyzed.

Salmon sperm DNA diluted stepwise from 10 μg to 1 μg with 2×SSC buffer was denatured with an alkali and was adsorbed to Hybond N+membrane (Amersham Biosciences) using Bio-Dot SF (BIO-RAD). After blocking the membrane with 5×Denhardt's solution (0.1% BSA, 0.1% ficoll, 0.1% polyvinylpyrrolidone), the membrane was immersed in 25 μg/mL of low-pI TM2 or the wild-type TM2 at room temperature for 90 minutes. Then, the membrane was washed with a TUBS buffer (TBS buffer containing 0.05% Tween 20) at room temperature for 5 minutes three times. The membrane was blocked with a TBS buffer containing 3% skimmed milk and 0.1% Tween 20 for 1 hour. The membrane was subjected to a reaction with biotinylated horseradise peroxidase (Vector) diluted 5000 times with a TBS buffer containing 3% skimmed milk and 0.1% Tween 20 at room temperature for 1 hour. The membrane was washed with a TBS buffer containing 0.1% Tween 20 again and was then shaken in a solution that is a mixture of reagent 1 and reagent 2 of ECL (Amasham) in the same volumes, followed by detection of the luminol reaction with Las-3000 (FUJIFILM).

Figure 3:
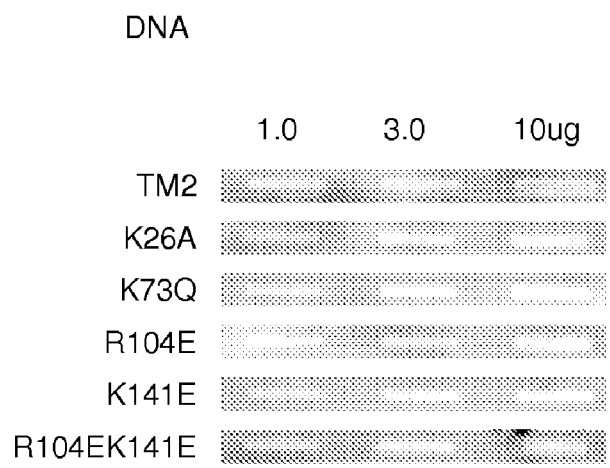
FIG. 3 shows non-specific binding of low-pI modified TM2 proteins of the present invention to DNA.

FIG. 3 shows the results. As shown in FIG. 3, only TM2 weakly bound to 10 µg of DNA, but the binding of every low-pI TM2 mutant was lower than the detection limit. This demonstrates that the non-specific binding of low-pI TM2 to DNA is significantly reduced.

On the basis of the results of Example 1, the properties of the low-pI modified TM2 of the present invention are summarized in Table 4.

TABLE 4

Summarized properties of low-pI modified TM2

|  | Binding of fluorescent biotin | pI | Non-specific binding of serum protein (%) | Binding of fibronectin (A450) | Non-specific binding of DNA |
|---|---|---|---|---|---|
| K19T | + | 6.6 to 7.5 |  |  |  |
| K26A | + | 7.3 to 7.6 | 68 | 0.85 | − |
| K73Q | + | 7.7 | 55 | 0.98 | − |
| R104E | + | 7.0 to 7.5 | 90 | 0.70 | − |
| K141E | + | 6.6 to 7.2 | 58 | 0.21 | − |
| K33T-K37A | + | 6.2 |  |  |  |
| K33T-K37A-R104E | + | 5.9 to 6.0 |  |  |  |
| R104E-K141E | + | 6.2 | 25 | 0.11 | − |
| TM2WT | + | 8.5 to 8.8 | 100 | 1.34 | ± |

Example 2

Construction and Analysis of High-affinity TM2

2-1) Construction of High-affinity TM2

In order to verify the enhancement of affinity to biotin, amino acid mutation was introduced into TM2.

Some streptavidins are publicly-known, for example, streptavidin v2 (Deposit Number: Q53533, Bayer, et al., (1995) Biochim Biophys Acta 1263: 60-66) and streptavidin v1 (Deposit Number: Q53532) from *Streptomyces violaceus*, and *Streptomyces avidinii* streptavidin (Deposit Number: P22629, Argarana, et al., (1986) Nucleic Acids Res 14: 1871-1882) from *Streptomyces avidinii*. As is described in WO02/072817, the amino acid sequence homologies of these streptavidins to the TM2 protein are each 50%, 48%, and 48%, i.e., about 50%.

The present inventors have supposed that a structure similar to that of streptavidin is necessary for maintaining or enhancing the biotin-binding ability of the TM2 protein. Accordingly, the amino acid sequences of streptavidin and TM2 were compared for the tryptophan residue, which is believed to play very important parts in binding between streptavidin and biotin, and residues that get involved in hydrogen bonds (Qureshi, et al., (2001), J. Biol. Chem. 276 (49), pp. 46422-46428).

As a result, the inventors have found that among the residues that got involved in hydrogen bonds with biotin, asparagine at position 49 of the streptavidin sequence was different from the corresponding amino acid (aspartic acid at position 40) in the TM2 sequence. The inventors have investigated whether or not the modification of D40 of TM2 to asparagine, i.e., to the streptavidin-type can enhance the affinity.

First, in order to construct high-affinity TM2, primers for introducing the above-mentioned mutation were designed: A Tm2NtermPci primer composed of the 5'-site of the TM2 gene and a sequence encoding PciI restriction enzyme cleavage site (ACATGT) located upstream of the 5'-site and a Tm2CtermBam primer composed of the 3'-site of the TM2 gene and a sequence encoding BamHI restriction enzyme cleavage site (GGATCC) located downstream of the 3'-site were the same as those described above. A series of sense primers containing mismatch codons for each mutant, and their antisense primers are as follows (SEQ ID NOs: 38 and 39):

TABLE 5

Primers for constructing high-affinity TM2

| Name Sequence (5'-3') | Length |
|---|---|
| TM2 SA D40N F<br>TAC CTC TCC AAA GTT GGG AAT GTC TAC GTG CCC TAC CCA | 39 mer |
| TM2 SA D40N R<br>TGG TGA GGG CAC GTA GAC ATT CCC AAC TTT GGA GAG GTA | 39 mer |

SEQ ID NOs: 38 and 39
The restriction enzyme recognition sites are underlined, and mutation sites are shown by dotted lines.

2-2) PCR and Cloning

As described above, a TM2 mutant in which aspartic acid at position 40 was replaced with asparagine (hereinafter referred to as "TM2 D40N"; its nucleotide sequence SEQ ID NO: 19, and the amino acid sequence in SEQ ID NO: 20) was constructed.

In order to construct a gene encoding this TM2 mutant, two-stage PCR was repeated. In the first-stage PCR, a plasmid of a pTrc99A vector containing a TM2 gene was used as a template, the 5'-site was amplified using a primer, Tm2NtermPci, and an antisense primer, TM2 SA D40N R, containing a mismatch codon of a mutant, while the 3'-site was amplified using a sense primer, TM2 SAD40N F, containing a mismatch codon and a primer, Tm2CtermBam.

The PCR was conducted under the reaction conditions: 50 μL of a reaction solution containing a template DNA (500 ng), 10× Pyrobest buffer (Takara, 5 μL), 2.5 mM dNTP (4 μL), primers (25 pmoles, each), and 5 U/μL Pyrobest DNA polymerase (Takara, 0.5 μL), and started with 3 min at 96° C. followed by ten cycles of 1 min at 96° C., 1 min at 55° C., and 2 min at 72° C., and ended with 6 min at 72° C. in a program temperature control system PC-700 (ASTEK). As a result, PCR products having supposed sizes were obtained in the 5'-site. These PCR products were subjected to agarose electrophoresis using low-melting-point agarose (SeaPlaque-GTG) in a TAE buffer for purifying the DNA fragments as described above.

Using these fragments as templates, the second-stage PCR was conducted using primers Tm2NtermPci and Tm2CtermBam. The reaction conditions were the same as those of the first-stage PCR. The resulting high-affinity TM2 gene fragment of 430 bp was cloned into a pCR4Blunt TOPO vector (Invitrogen) by the same process as above. As a result, a TM2 D40N protein-expressing vector, TM2 D40N/pTrc99A, was obtained.

2-3) Expression of High-Affinity TM2 in *Escherichia coli*

*Escherichia coli* TB1 transformed with the pTrc99A vector containing the TM2 mutant produced in the 2-2) was inoculated into an LB culture medium (6 mL) containing an antibiotic, ampicillin (final concentration: 100 μg/mL), and was cultured with shaking at 37° C. until the absorbance at 600 nm, $OD_{600}$, reached 0.5.

Subsequently, 1 mM IPTG was added to the culture solution, followed by shaking culture at 37° C. overnight. *Escherichia coli* was collected from 1 mL of the culture solution by centrifugation and was suspended in 20 mM phosphate buffer (pH 7, 400 μL), followed by disruption of bacterial cells by sonication. The disruption solution was centrifuged (15000 rpm) to collect a soluble fraction as the supernatant. The soluble fraction was subjected to western blotting analysis: The soluble fraction and the same volume of 2×SDS sample buffer were mixed and were heated at 95° C. for 10 minutes, followed by separation by SDS-PAGE for western blotting analysis using anti-TM2 rabbit antibody (PCT/JP2006/326260) as the primary antibody and alkaline phosphate-labeled anti-rabbit IgG antibody (BIO-RAD) as the secondary antibody.

As a result, a band near 15.5 kDa was detected in *Escherichia coli* transformed with a pTrc99A vector containing TM2 D40N, but was not detected in *Escherichia coli* transformed with a pTrc99A vector not containing the TM2 mutant. The size of the band agreed with the molecular weight, 15.5 kDa, of a monomer predicted from the amino acid sequence of TM2. Then, as in low-pI TM2, the formation of a tetramer of high-affinity TM2 in the nondenatured state was confirmed in accordance with the method by Bayer, et al., (1996, Electrophoresis, 17(8), 1319-24). The results showed a band having the same size as that of the wild type TM2 in the high-affinity TM2, which demonstrated the formation of the tetramer. The expression level of a soluble TM2 protein was 20 mg for 1 L of the culture solution.

2-4) Purification of High-Affinity TM2

The high-affinity TM2 was purified in accordance with the method by Hofmann, et al., (1980) as described above. As a result, the amount of purified TM2 mutant protein was substantially the same level as the amount expressed in *Escherichia coli* to show a purity of 95% or more.

2-5) Measurement of Activity by Fluorescent Biotin

The biotin-binding ability of purified TM2 mutant was confirmed in accordance with the method in Biochim. Biophys. Acta, 1427, 44-48 (1999). The results showed that the fluorescent intensity decreased in proportion to the increase in the amount of the TM2 mutant solution. This verified that the D40N mutation does not significantly inhibit the binding between TM2 and a biotin-like compound.

2-6) Isoelectric Focusing Electrophoresis

The isoelectric point of the high-affinity TM2 was measured by isoelectric focusing electrophoresis using an XCell SureLock Mini-Cell (Invitrogen). Table 6 shows the analytical results of the high-affinity TM2 (200 ng) in accordance with the instruction. The electric point of TM2 D40N having replacement of the basic amino acid was higher than that of the wild type TM2 also in the isoelectric focusing electrophoresis.

TABLE 6

Isoelectric point of high-affinity TM2

| Sample Name | pI calculated | pI observed |
|---|---|---|
| TM2 D40N | 8.6 | 9.7 |
| TM2 | 7.4 | 8.5 to 8.8 |

2-7) Measurement of Biotin-Binding Ability

The intermolecular interaction was analyzed by an iminobiotin binding test and a biotin binding test of the high-affinity TM2 using a Biacore 3000 (Biacore).

2-7-1) Iminobiotin Binding Test

TM2 and high-affinity TM2 that were used as ligands to be attached to sensor chips were purified with 2-iminobiotin agarose in accordance with a common process and were dialyzed with 20 mM KPi (pH 7) overnight. These samples were diluted with 10 mM acetate buffer (pH 5, Biacore) into about 50 μg/mL.

Immobilization was performed at 25° C. and a flow rate of 10 μL/min using HBS-EP (Biacore) as a running buffer. The TM2 and the TM2 mutant (about 4000 to 8000 RU) were immobilized on CM5 sensor chips (Biacore) by amine coupling. The activating time was set to 10 minutes.

The specific interaction was measured using iminobiotin BSA as an analyte (a material flowing in a flow channel) at 25° C. and a flow rate of 20 μL/min and using a CAPS buffer (50 mM CAPS, 150 mM NaCl, 0.005% Tween 20, pH 11) as the running buffer. Iminobiotin BSA was produced as follows: A highly purified BSA (Sigma, 2 mg) and NHS-iminobiotin (Pierce, 1 mg) were dissolved in 50 mM sodium borate (pH 8.0, 1 mL), followed by incubation at 4° C. for 2 hours. The solution was put into a dialysis tube (MWCO 6-8,000) and was dialyzed with 50 mM sodium carbonate (pH 6.7) at 4° C. overnight. The resulting iminobiotin-BSA conjugate (MW: 67 kDa, 30 μM) was used as an analyte for a Biacore (registered trademark) biosensor. The injection time of the iminobiotin-BSA was 2 minutes, and the dissociation time was 10 minutes. The measurement was performed by increasing the concentration stepwise from a low concentration without recycling steps. First, 40 μL of BSA diluted with the running buffer to 9.375 nM, 18.75 nM, 37.5 nM, 75 nM, 150 nM, 300 nM, and 600 nM was injected (2 minutes) from the lower concentration into a flow cell to which an objective protein was immobilized to measure the dissociation. Subsequently, the iminobiotin-BSA produced by the process described above was similarly measured with the same flow cell.

Each constant of samples showing interaction was calculated using analysis software BIAevaluation ver. 4.1. The sensorgram obtained in BSA as the reference at the same concentration as that of iminobiotin-BSA was deducted from the sensorgram obtained in the iminobiotin-BSA at each concentration, and the resulting sensorgram was subjected to reaction kinetics analysis using a 1:1 (Langmuir) binding model to calculate the binding rate constant (ka) and the dissociation rate constant (kd). The dissociation constant (KD) was determined from kd/ka. In the case where no recycling step is employed, the Rmax (maximum amount of binding analyte) decreases at each measurement. Accordingly, in the analysis, the Rmax was calculated by conducting local fitting for each concentration, and only the results at concentrations (mainly 18.75 to 75 nM) approximated to the 1:1 (Langmuir) binding model were employed.

As a result, the binding rate constant (ka) of TM2 D40N to iminobiotin was increased by 40% and the dissociation rate constant (kd) was decreased by 45% compared to TM2, which caused a reduction in KD by about 60%. That is, the affinity of TM2 D40N to iminobiotin was 2.5 times that of TM2 (Table 7).

2-7-2) Biotin-Binding Test

High-purity BSA (Sigma, 2 mg) and NHS-LC-biotin (Pierce, 1 mg) were dissolved in 50 mM sodium borate (pH 8.0, 1 mL) and were incubated at 4° C. for 2 hours. The solution was put into a dialysis tube (MWCO 6-8,000) and was dialyzed with 50 mM sodium carbonate (pH 6.7) at 4° C. overnight. The resulting biotin-LC-BSA conjugate (MW: 67 kDa, 30 μM) was used as a ligand for a Biacore (registered trademark) biosensor. Aside from this, TM2 and high-affinity TM2 (D40N) were purified using 2-iminobiotin agarose as described above and were dialyzed with 20 mM KPi (pH 7) overnight to prepare analytes.

Biotin-LC-BSA and BSA serving as a negative control were immobilized on CM5 sensor chips by amine coupling method. The amount for immobilization was adjusted to about 200 RU. The chips to which BSA was immobilized were disposed in flow cells 1 and 3, while the chips to which biotin-LC-BSA was immobilized were disposed in flow cells 2 and 4. The flow cells 1 and 2 were loaded with TM2, while the flow cells 3 and 4 were loaded with high-affinity TM2 (D40N), at a flow rate of 20 μL/min for 2 minutes using a running buffer [10 mM HEPES, pH 7.4, 150 mM NaCl, 3 mM EDTA, 0.005% Surfactant 20 (Biacore)].

Then, dissociation of the samples was monitored for 60 minutes, but the bound TM2 and high-affinity TM2 (D40N) were not dissociated. Accordingly, seven step measurement (3.125, 6.25, 125, 25, 50, 100, and 200 nM) was conducted from the lowest concentration, without recycling steps. The data of BSA as reference was deducted from the data of BSA-LC-biotin. The measurement was performed at 25° C. The resulting sensorgrams were subjected to reaction kinetics analysis using analysis software BIAevaluation ver. 4.1 with a 1:1 binding model to calculate the binding rate constant (ka) and the dissociation rate constant (kd). The dissociation constant (KD) was determined from kd/ka. In the case where no recycling step is employed, the Rmax (maximum amount of binding analyte) decreases at each measurement. Accordingly, in the analysis, the Rmax was calculated by conducting local fitting for each concentration, and only the data of analyte concentrations that were approximated to the 1:1 binding model was employed.

As a result, the binding rate constant (ka) of TM2 D40N increased and the dissociation rate constant (kd) decreased, compared to those of TM2 (Table 7).

These results demonstrate that the biotin-binding ability (affinity) of TM2 D40N was enhanced.

TABLE 7

Analysis of interaction between high-affinity TM2, iminobiotin, and biotin

| Sample name | ka(1/Ms) | kd(1/s) |
| --- | --- | --- |
| Iminobiotin-BSA | | |
| TM2D40N | $1.8 \pm 0.6 \times 10^5$ | $6.9 \pm 1.0 \times 10^{-4}$ |
| TM2 | $1.3 \pm 0.5 \times 10^5$ | $1.3 \pm 0.6 \times 10^{-3}$ |
| Biotin-LC-BSA | | |
| TM2D40N | $1.1 \times 10^6$ | $(1.8 \times 10^{-8})$ |
| TM2 | $9.9 \times 10^5$ | $(1.2 \times 10^{-6})$ |

On the basis of the results of Example 2, the properties of the high-affinity TM2 of the present invention are summarized in Table 8.

TABLE 8

Summarized properties of high-affinity TM2

| | Binding of Fluorescent biotin | Affinity analysis by Biacore (KD (M) = kd/ka) | |
| --- | --- | --- | --- |
| | | KD to iminobiotin | KD to biotin |
| D40N | + | $4.0 \pm 1.2 \times 10^{-9}$ | $1.7 \times 10^{-14}$ |
| TM2 | + | $9.8 \pm 4.7 \times 10^{-9}$ | $1.3 \times 10^{-11}$ |

Example 3

Construction and Analysis of Low-non-specific Binding/High-Affinity TM2

3-1) Construction of Low-non-specific Binding/High-Affinity TM2 (HALU TM2: High Affinity and Low Non-Specificity)

Mutation for decreasing non-specific binding and also increasing affinity to biotin was introduced into TM2.

As mutation for decreasing non-specific binding, on the basis of the results in Example 1, mutations of R104E and K141E were introduced as amino acid mutation for reducing non-specific binding. As mutation for increasing the affinity to biotin, on the basis of the results of biotin-binding ability measured in Example 2, the mutation of D40N was introduced. That is, constructed were a TM2 mutant having mutation of D40N and R104E (hereinafter referred to as "TM2 D40NR104E"; its nucleotide sequence is listed in SEQ ID NO: 21, and the amino acid sequence in SEQ ID NO: 22) and a TM2 mutant having mutation of D40N and R104EK141E (hereinafter referred to as "TM2 D40NR104EK141E"; its nucleotide sequence is listed in SEQ ID NO: 23, and the amino acid sequence in SEQ ID NO: 24).

3-2) PCR and Cloning

The same primers used for introduction of each mutation were used for construction of HALU TM2. The PCR conditions and cloning were performed by the same processes as described above.

A gene encoding TM2 D40NR104E was constructed by producing a TM2 D40NR104E/pTrc99A vector for expressing a TM2 D40NR104E protein by introduction of mutation through two-stage PCR reaction using a TM2 D40N/pTrc99A vector as a template and using a primer pair of Tm2NtermPci and Tm2 R104E R and a primer pair of Tm2 R104E F and Tm2CtermBam. A gene encoding TM2 D40NR104EK141E was constructed by producing a TM2 D40NR104EK141E/pTrc99A vector for expressing a TM2 D40NR104EK141E protein by introduction of mutation through one-stage PCR reaction using a TM2 D40NR104E/pTrc99A vector as a template and using a primer pair of Tm2NtermPci and Tm2 K141E Bam.

3-3) Expression of HALU TM2 by *Escherichia coli*

*Escherichia coli* TB1 transformed with a pTrc99A vector containing any of TM2 mutants was inoculated into an LB culture medium (6 mL) containing an antibiotic, ampicillin (final concentration: 100 μg/mL) and was cultured with shaking at 37° C. or 25° C. until the absorbance at 600 nm, $OD_{600}$, reached to 0.5. 1 mM IPTG was added and further culture was shaken at 37° C. or 25° C. overnight. *Escherichia coli* was collected from 1 mL of the culture solution by centrifugation and was suspended in 20 mM phosphate buffer (pH 7, 400 μL), followed by disruption of bacterial cells by sonication. The disruption solution was centrifuged (15000 rpm) to obtain a soluble fraction as the supernatant. This soluble fraction and the same volume of 2×SDS sample buffer were mixed and were heated at 95° C. for 10 minutes. Proteins were separated by SDS-PAGE and were detected by CBB staining.

As a result, a band near 15.5 kDa was detected in every *Escherichia coli* transformed with a pTrc99A vector containing a TM2 mutant, but was not detected in *Escherichia coli* transformed with a pTrc99A vector not containing the TM2 mutant. The sizes of these bands agreed with the molecular weight, 15.5 kDa, of a monomer predicted from the amino acid sequence of TM2. Then, as in the low-pI TM2 and the high-affinity TM2, the formation of a tetramer of HALU TM2 in the nondenatured state was confirmed in accordance with the method by Bayer, et al., (1996, Electrophoresis, 17(8), 1319-24). The results showed a band having the same size as that of the wild type TM2 in the HALU TM2, which demonstrated the formation of the tetramer. The expression levels of soluble TM2 mutant proteins for 1 L of the culture solution were 24 mg in culture of TM2 D40NR104E at 37° C., 10 mg in culture of TM2 D40NR104EK141E at 37° C., and 32 mg in culture of TM2 D40NR104E at 25° C. In terms of TM2 D40NR104EK141E, a change of the host cells to BL21 (DE3) increased the expression level of the soluble fraction in culture at 25° C. to 43 mg.

3-4) Purification of HALU TM2

HALU TM2 was purified in accordance with the method by Hofmann, et al. (1980) described above. As a result, the amount of purified protein of each TM2 mutant was substantially the same level as the amount expressed in *Escherichia coli* to show a purity of 90% or more.

3-5) Measurement of Activity by Fluorescent Biotin

The biotin-binding ability of each purified TM2 mutant was confirmed in accordance with the method in Biochim. Biophys. Acta, 1427, 44-48 (1999). The results demonstrated that the fluorescent intensity decreased in proportion to the increase in the amount of the HALU TM2 mutant solution. This confirmed that the HALU TM2 mutant bound to a biotin-like compound.

3-6) Isoelectric Focusing Electrophoresis

The isoelectric point of HALU TM2 was measured by isoelectric focusing electrophoresis using an XCell SureLock Mini-Cell (Invitrogen). In accordance with the instruction, bands of each HALU TM2 (4 µg) were detected by CBB staining. Table 9 shows the results. The observed isoelectric point of TM2 D40N was 9.7, and was reduced to 8.9 after introduction of mutation of R104E and was reduced to 7.3 to 7.5 after further introduction of mutation of K141E.

TABLE 9

Isoelectric point of HALU TM2

| Sample name | pI calculated | pI observed |
|---|---|---|
| TM2 D40NR104E | 6.3 | 8.9 |
| TM2 D40NR104EK141E | 5.4 | 7.3 to 7.5 |

3-7) Measurement of Biotin-binding Ability

A biotin binding test of the high-affinity TM2 was conducted using a Biacore 3000 (Biacore).

Biotin BSA used as a ligand was prepared as described in paragraph 2-7-2). TM2 and HALU TM2 used as analytes were prepared by purification with 2-iminobiotin agarose in accordance with a common method and dialysis with 20MM KPi (pH 7) overnight. The analytes were each adjusted to about 50 µg/mL in 10 mM acetate buffer (pH 5, Biacore).

The immobilization of the ligand and measurement and analysis of specific interaction with the analytes were conducted as in paragraph 2-7-2). As a result, the binding rate constant (ka) to biotin increased in both HALU TM2 mutants compared to TM2. In TM2 D40NR104EK141E, the dissociation rate constant (kd) decreased, demonstrating a further enhancement in the biotin-binding ability.

TABLE 10

Analysis of interaction between high-affinity TM2 and biotin
Biotin-BSA (22.4 Å)

| Sample Name | ka | kd | KD |
|---|---|---|---|
| TM2 D40NR104E | $1.4 \times 10^6$ | $(2.9 \times 10^{-9})$ | $(2.2 \times 10^{-15})$ |
| TM2 D40NR104EK141E | $1.5 \times 10^6$ | $(1.4 \times 10^{-8})$ | $(9.3 \times 10^{-15})$ |
| TM2 | $9.9 \times 10^5$ | $(1.2 \times 10^{-6})$ | $(1.3 \times 10^{-12})$ |

3-8) Heat Stability of HALU TM2 Protein Structure Each of 0.2 µg/µL TM2 mutant solutions (10 µL (2 µg)) was heated at room temperature, 50, 60, 70, 80, 90, or 99° C. for 20 minutes. Then, the solution was centrifuged at 15000 rpm for 10 minutes, and the soluble protein in the supernatant was suspended in the same volume of 2×SDS sample buffer (250 mM Tris-HCl, pH 6.8, 20% 2-mercaptoethanol, 20% SDS, 20% glycerol). The suspension was heated at 95° C. for 10 minutes, followed by SDS-PAGE. The protein bands were detected by CBB staining A standard curve was prepared using a quantitative marker (LMW ELECTROPHORESIS CALIBRATION KIT; Pharmacia Biotech) with Las-3000 (FUJIFILM) to quantify the protein bands.

As a result, the temperature at which 50% of the D40NR104E protein was lost was 78° C. On the contrary, 78% of the D40NR104EK141E protein remained even if the protein was heated at 99° C. The temperature at which 50% of protein was lost was 87.5° C. in TM2 and 70° C. in streptavidin.

3-9) Non-Specific Binding of HALU TM2 to Human Serum

In this Example, non-specific adsorption of serum protein to HALU TM2-immobilized magnetic beads was investigated.

TM2 D40NR104E and TM2 D40NR104EK141E were bonded covalently to magnetic beads (Dynabeads M-270 Carboxylic Acid, Dynal) by the process described in paragraph 1-9) of Example 1, and the amount of human serum protein adsorbed to the beads was measured. The amount of each HALU TM2 immobilized to the magnetic beads was adjusted to 10 µg/100 µL beads. Human serum (CHEMICON) was diluted 800 times with a PBS buffer, and the HALU TM2-immobilized magnetic beads (50 µL) to which a certain amount of protein was immobilized were added to the diluted human serum, followed by mixing by turning the tube containing the beads upside down at room temperature for 15 minutes. The magnetic beads were washed with a PBS buffer containing 0.1% Tween 20 (PBST, 500 µL) four times and were then subjected to antigen-antibody reaction at room temperature for 15 minutes with HRP-labeled anti-human IgG mouse antibody (100 µL) diluted 5000 times with PBST containing 0.5% BSA. Subsequently, the beads were washed with PBST (500 µL) five times, followed by color development with 1-Step Ultra TMB-ELISA (100 µL). After termination of the color development with 2M sulfuric acid (100 µL), the magnetic beads were collected with a magnet. The absorbance at 450 nm of the supernatant was measured with an Infinite 200 microplate reader.

Figure 4:
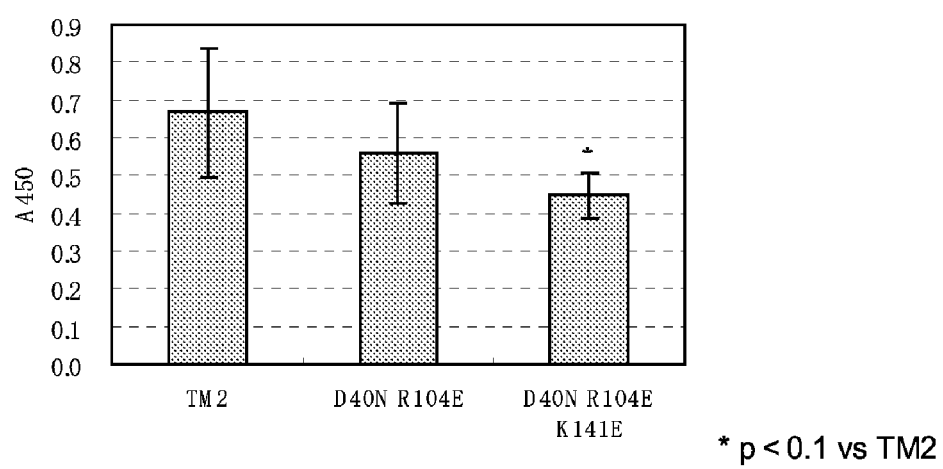
FIG. 4 shows non-specific adsorption of serum protein to magnetic beads immobilizing the low-non-specific binding/high-affinity TM2 protein of the present invention (* $p<0.1$ vs TM2).

FIG. 4 shows the results. As shown in FIG. 4, the non-specific binding was low in both TM2 D40NR104E and TM2 D40NR104EK141E compared to the wild type TM2-immobilized magnetic beads.

3-10) Non-specific Binding to Fibronectin

Non-specific binding of HALU TM2 to fibronectin was also investigated as in paragraph 1-10) of Example 1.

Figure 5:
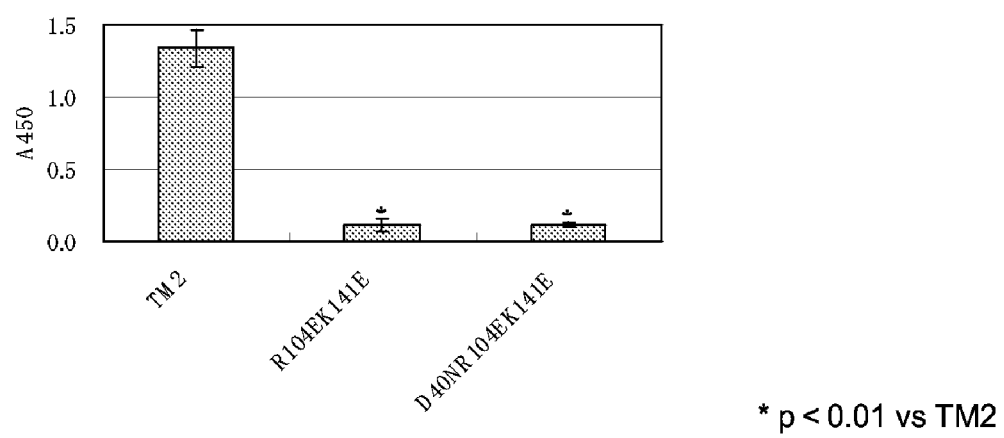
FIG. 5 shows non-specific binding of low-non-specific binding/high-affinity TM2 proteins of the present invention to fibronectin (* $p<0.01$ vs TM2).

The results demonstrated that the binding of TM2 D40NR104EK141E to fibronectin was also extremely low, and thus was significantly lower than that of TM2 (FIG. 5). The inhibition effect of D40NR104EK141E on binding to fibronectin was comparable with that of TM2 R104EK141E exhibiting the highest effect among the low-pI TM2 mutants.

This result revealed that the D40N mutation does not affect the binding of R104EK141E to fibronectin.

3-11) Non-Specific Binding to DNA

Figure 6:
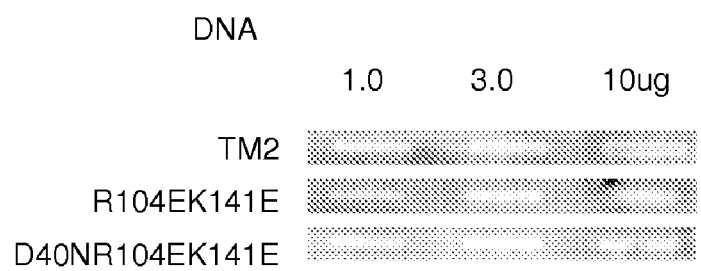
FIG. 6 shows non-specific binding of low-non-specific binding/high-affinity TM2 proteins of the present invention to DNA, wherein the upper, middle, and lower columns show the results of the wild-type TM2, TM2 R104EK141E, and TM2 D40NR104EK141E, respectively.

The non-specific binding of HALU TM2 to DNA was analyzed by the process in paragraph 1-11) of Example 1. The results demonstrated that the binding of TM2 D40NR104EK141 to 10 μg DNA was lower than the detection limit, as in TM2 R104EK141E, whereas the wild type TM2 weakly bound (FIG. 6). This demonstrates that D40N mutation does not affect the binding to DNA.

On the basis of the results of Example 3, properties of low-non-specific binding/high-affinity TM2 of the present invention are summarized in Table 11.

TABLE 11

| | Summarized properties of low-non-specific binding/high-affinity TM2 | | | | | | |
|---|---|---|---|---|---|---|---|
| | Binding of fluorescent biotin | pI | Biacore analysis (KD) | Thermal stability (temp. at which 50% of protein was lost) | Non-specific binding to serum protein (A450) | Binding to fibronectin (A450) | Non-specific binding to DNA |
| D40NR104E | + | 8.9 | $2.2 \times 10^{-15}$ | 78° C. | 0.56 | NT | NT |
| D40NR104EK141E | + | 7.3 to 7.5 | $9.3 \times 10^{-15}$ | 99° C. or more | 0.45 | 0.12 | − |
| TM2WT | + | 8.5 to 8.8 | $1.3 \times 10^{-12}$ | 86° C. | 0.67 | 1.34 | ± |

NT: Not tested

The invention claimed is:

1. A modified tamavidin-2 biotin-binding protein, comprising an amino acid sequence having 80% or more identity to the sequence represented by SEQ ID NO: 2, wherein said modified biotin-binding protein having one or more amino acid residues replaced with an acidic amino acid residue or a neutral amino acid residue, said one or more amino acid residues selected from the group consisting of: the arginine residue at position 104 of SEQ ID NO: 2; the lysine residue at position 141 of SEQ ID NO: 2; the lysine residue at position 26 of SEQ ID NO: 2; and the lysine residue at position 73 of SEQ ID NO: 2, wherein said modified tamavidin-2 biotin-binding protein has biotin binding activity.

2. The modified biotin-binding protein according to claim 1, wherein the selected amino acid residue is replaced with an amino acid residue having a hydropathy index of 2 or less.

3. The modified tamavidin-2 biotin-binding protein according to claim 1, wherein the arginine residue at position 104 of SEQ ID NO: 2 and/or the lysine residue at position 141 of SEQ ID NO: 2 is replaced with an acidic amino acid residue or a neutral amino acid residue.

4. The modified tamavidin-2 biotin-binding protein according to claim 3, wherein the arginine residue at position 104 of SEQ ID NO: 2 and/or the lysine residue at position 141 of SEQ ID NO: 2 is replaced with an acidic amino acid residue.

5. The modified tamavidin-2 biotin-binding protein according to claim 3, wherein the arginine residue at position 104 of SEQ ID NO: 2 and/or the lysine residue at position 141 of SEQ ID NO: 2 is replaced with a glutamic acid residue.

6. The modified tamavidin-2 biotin-binding protein according to claim 1, further comprising the replacement of the aspartic acid residue at position 40 of SEQ ID NO: 2 with an asparagine residue.

7. The modified tamavidin-2 biotin-binding protein according claim 6, which is selected from the group consisting of:
   a modified biotin-binding protein (D40N-R104E) in which an aspartic acid residue at position 40 of SEQ ID NO: 2 is replaced with an asparagine residue, and an arginine residue at position 104 is replaced with a glutamic acid residue;
   a modified biotin-binding protein (D40N-K141 E) in which an aspartic acid residue at position 40 of SEQ ID NO: 2 is replaced with an asparagine residue, and a lysine residue at position 141 is replaced with a glutamic acid residue; and
   a modified biotin-binding protein (D40N-R104E-K141E) in which an aspartic acid residue at position 40 of SEQ ID NO: 2 is replaced with an asparagine residue, an arginine residue at position 104 is replaced with a glutamic acid residue, and a lysine residue at position 141 is replaced by a glutamic acid residue.

8. The modified tamavidin-2 biotin-binding protein according to claim 1, further comprising:
   a) the asparagine residue at position 14 of SEQ ID NO: 2 is not modified or is replaced with glutamine or aspartic acid;
   b) the serine residue at position 18 of SEQ ID NO: 2 is not modified or is replaced with threonine or tyrosine;
   c) the tyrosine residue at position 34 of SEQ ID NO: 2 is not modified or is replaced with serine, threonine, or phenylalanine;
   d) the serine residue at position 36 of SEQ ID NO: 2 is not modified or is replaced with threonine or tyrosine;
   e) the aspartic acid residue at position 40 of SEQ ID NO: 2 is not modified or is replaced with asparagine;
   f) the tryptophan residue at position 69 of SEQ ID NO: 2 is not modified;
   g) the serine residue at position 76 of SEQ ID NO: 2 is not modified or is replaced with threonine or tyrosine;
   h) the threonine residue at position 78 of SEQ ID NO: 2 is not modified or is replaced with serine or tyrosine;
   i) the tryptophan residue at position 80 of SEQ ID NO: 2 is not modified;
   j) the tryptophan residue at position 96 of SEQ ID NO: 2 is not modified;
   k) the tryptophan residue at position 108 of SEQ ID NO: 2 is not modified; and
   l) the aspartic acid residue at position 116 of SEQ ID NO: 2 is not modified or is replaced with glutamic acid or asparagine.

9. The modified tamavidin-2 biotin-binding protein according to claim 1, comprising an amino acid sequence having 90% or more identity to the sequence represented by SEQ ID NO: 2.

10. The modified tamavidin-2 biotin-binding protein according to claim 1, having at least one property selected from the following properties i) to iv):
    i) having an isoelectric point lower than that of a protein consisting of an amino acid sequence represented by SEQ ID NO: 2;
    ii) showing less non-specific binding to nucleic acids and/or proteins compared to a protein consisting of an amino acid sequence represented by SEQ ID NO: 2;
    iii) showing less fibronectin-binding activity compared to a protein consisting of an amino acid sequence represented by SEQ ID NO: 2; and
    iv) showing more biotin-binding activity compared to a protein consisting of an amino acid sequence represented by SEQ ID NO: 2.

11. A modified tamavidin-2 biotin-binding protein, comprising an amino acid sequence having 80% or more identity to the sequence represented by SEQ ID NO: 2, wherein the aspartic acid residue at position 40 of SEQ ID NO: 2 is replaced with an asparagine residue, wherein said modified tamavidin-2 biotin-binding protein has biotin binding activity.

12. The modified tamavidin-2 biotin-binding protein according to claim 11, wherein the biotin-binding activity is higher than that of a protein consisting of the amino acid sequence represented by SEQ ID NO: 2.

13. A nucleic acid encoding the protein of claim 1.

14. A vector containing the nucleic acid according to claim 13.

15. A carrier to which the protein according to claim 1 is immobilized.

* * * * *